United States Patent
Bornhop et al.

(10) Patent No.: US 8,367,714 B2
(45) Date of Patent: Feb. 5, 2013

(54) CANNABINOID RECEPTOR TARGETED AGENT

(75) Inventors: Darryl J. Bornhop, Nashville, TN (US); Mingfeng Bai, Bridgeville, PA (US); Nephi Stella, Seattle, WA (US); Eric Stern, Saint-Quentin (FR)

(73) Assignees: Vanderbilt University, Nashville, TN (US); University of Washington, Seattle, WA (US)

( * ) Notice: Subject to any disclaimer, the term of this patent is extended or adjusted under 35 U.S.C. 154(b) by 867 days.

(21) Appl. No.: 12/200,732

(22) Filed: Aug. 28, 2008

(65) Prior Publication Data

US 2009/0105128 A1 Apr. 23, 2009

Related U.S. Application Data

(60) Provisional application No. 60/968,516, filed on Aug. 28, 2007.

(51) Int. Cl.
A61K 31/415 (2006.01)
C07D 231/14 (2006.01)
(52) U.S. Cl. .................... 514/406; 548/374.1
(58) Field of Classification Search .............. 514/406; 548/374.1
See application file for complete search history.

(56) References Cited

U.S. PATENT DOCUMENTS

| | | | |
|---|---|---|---|
| 5,925,768 | A | 7/1999 | Barth et al. |
| 7,338,651 | B2 | 3/2008 | Bornhop et al. |
| 7,754,884 | B2 | 7/2010 | Bornhop et al. |
| 2008/0031823 | A1 | 2/2008 | Bornhop et al. |
| 2008/0241074 | A1 | 10/2008 | Bornhop et al. |
| 2008/0241873 | A1 | 10/2008 | Bornhop et al. |
| 2009/0105128 | A1 | 4/2009 | Bornhop et al. |
| 2010/0278739 | A1 | 11/2010 | Bornhop et al. |
| 2010/0324130 | A1 | 12/2010 | Bornhop et al. |

FOREIGN PATENT DOCUMENTS

| | | |
|---|---|---|
| AU | 2002323528 | 3/2008 |
| CA | 2459724 | 2/2011 |
| EP | 1429783 | 6/2004 |
| EP | 1841466 | 10/2007 |
| WO | WO03020701 | 3/2003 |
| WO | WO2006074129 | 7/2006 |

OTHER PUBLICATIONS

Bai et al. "MBC94, a Conjugable Ligand for Cannabinoid CB2 Receptor Imaging" Bioconjugate Chemistry, 2008, vol. 19, pp. 988-992.*
Bai, M.; Sexton, M.; Stella, N.; Bornhop, D. J. "MBC94, a conjugable Ligand for cannabinoid CB.sub.2 receptor imaging" Bioconjugate Chem. 2008, 19, 988-992.
Katz, H. E. "Chelate and macrocycle effects in the 2,2'-bipyridine N,N-dioxide complexation of alkyltin trichlorides" J. Org. Chem. 1985, 50, 2086-2091.
Narayanan, N. and Patonay, G. "A New Method for the Synthesis of Heptamethine Cyanine Dyes: Synthesis of New Near-Infrared Fluorescent Labels" J. Org. Chem. 1995, 60, 2391-2395.
Pommery, N.; Taverne, T.; Telliez, A.; Goossens, L.; Charlier, C.; Pommery, J.; Goossens, J.-F.; Houssin, R.; Durant, F.; Henichart, J.-P. "New COX-2/5-LOX inhibitors: apoptosis-inducing agents potentially useful in prostate cancer chemotherapy" J. Med. Chem. 2004, 47, 6195-6206.
Roy, A. K.; Batra, S. (2003) Facile Baylis-Hillman reaction of substituted 3-isoxazolecarbaldehydes: The impact of a proximal heteroatom within a heterocycle on the acceleration of the reaction. Synthesis-Stuttgart 2325-2330.
Seltzman, H. H.; Foster, M. C.; Wyrick, C. D.; Burgess, J. P.; Carroll, F. I. "Tritiation of the cannabinoid receptor antagonist SR144528 involving lithium aluminum tritide reduction; assessment of the kinetic isotope effect by 3H-NMR" J. Label. Compd. Radiopharm. 2005, 48, 589-596.
Suchocki, J. A.; May, E. L.; Martin, T. J.; George, C.; Martin, B. R. "Synthesis of 2-exo- and 2-endo-mecamylamine analogues. Structure-activity relationships for nicotinic antagonism in the central nervous system" J. Med. Chem. 1991, 34, 1003-1010.
Walker, J. R.; Alshafie, G.; Nieves, N.; Ahrens, J.; Clagett-Dame, M.; Abou-Issa, H.; Curley Jr., R. W. "Synthesis and preliminary chemotherapeutic evaluation of the fully C-linked glucuronide of N-(4-hydroxyphenyl)retinamide" Bioorg. Med. Chem. 2006, 14, 3038-3048.

* cited by examiner

*Primary Examiner* — Joseph Kosack
(74) *Attorney, Agent, or Firm* — Stites & Harbison, PLLC; Richard S. Myers, Jr.

(57) ABSTRACT

Compounds of the following formula:

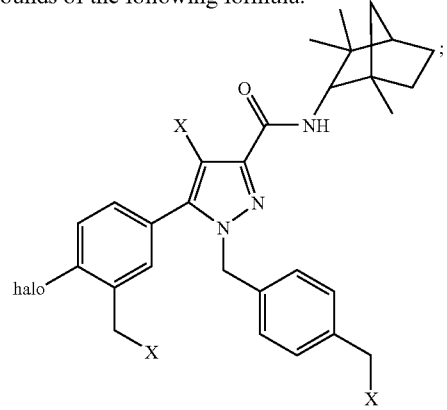

wherein X is H or substituted with

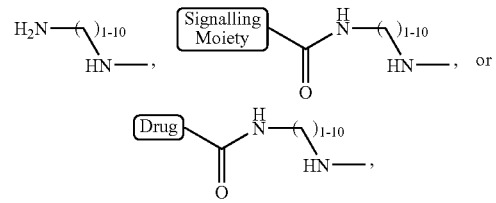

with at least one X being substituted; and halo is fluorine, chlorine, bromine, iodine; and stereoisomers and conjugable analogs thereof.

32 Claims, 4 Drawing Sheets

CANNABINOID RECEPTOR TARGETED AGENT

PRIORITY INFORMATION

This application claims benefit to U.S. Patent Application No. 60/968,516, filed Aug. 26, 2007, the contents of which are incorporated herein by reference in their entirety.

GOVERNMENT SUPPORT

This invention was made with support from the Department of Defense contract number W81XWH-04-1-0432 and the National Institute of Health grant number DA014486. The US Government has rights to this invention.

BACKGROUND OF THE INVENTION

Two distinct cannabinoid receptors have been identified in mammalian tissues: cannabinoid (CB1) receptor is mainly located in the central nervous system, whereas CB2 receptor is primarily expressed by immune and tumor cells.

The high level of $CB_2$ receptor expression in immune cells and much lower expression in other cell types, particularly in the CNS, makes this receptor an attractive target for imaging and monitoring of therapy for neurological diseases. Specifically, $CB_2$ receptor expression is high in spleen, tonsils and thymus, and low—or even undetectable—in brain, thyroid, retina, placenta, skeletal muscle, kidney, liver, adrenal gland, heart, prostate and ovary. This expression profile provides great opportunities for imaging with low background. Furthermore, $CB_2$ receptor expression is highly plastic and may be induced under specific disease conditions, for example in tumor cells and CNS-resident microglia. Accordingly, $CB_2$ receptor has become a predominant target for drug development aimed at treating pain, chronic inflammation, osteoporosis, malignant gliomas, tumors of immune origin and immunological disorders, and thus developing tool that allow for its precise mapping in tissue and for identifying novel CB2 receptor specific ligands is desired.

Together with the characterization of the $CB_2$ receptor, a considerable effort has been made to develop $CB_2$ receptor ligands. The term cannabinoid was first used to describe terpenophenolic compounds in *Cannabis Sativa* L., among which (−)-trans-$\Delta^9$-tetrahydrocanabinol ($\Delta^9$-THC) is the main bioactive constituent. Many anti-inflammatory effects of $\Delta^9$-THC have been described, including inhibition of tumor necrosis factor-α, interleukin-2, nitric oxide and arachidonic acid production from macrophages and T cells, $CB_2$ receptor ligands can be divided into three main groups: plant-derived, endogenous and synthetic. The best-known plant-derived cannabinoid is $\Delta^9$-THC, but cannabinol and cannabidiol also induce profound biological effects. Two endocannabinoids, arachidonoylethanolamide (anandamide) and 2-arachidonoyl glycerol (2-AG), have been identified.

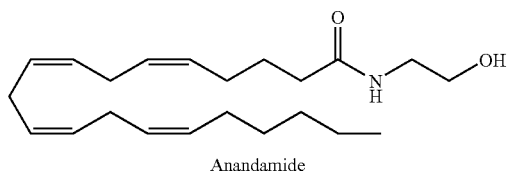

Anandamide

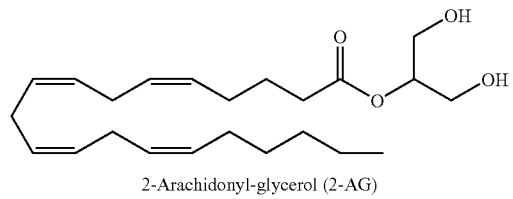

2-Arachidonyl-glycerol (2-AG)

Both molecules above have greater affinity at $CB_1$ than $CB_2$ receptors. 2-AG acts as a full agonist at $CB_1$ and $CB_2$ receptor, and anandamide acts as a partial agonist (showing mixed agonist-antagonist properties) toward these receptors. Many synthetic cannabinoid receptor ligands have been developed, including HU-210, CP55940, WIN55212-2, SR141617A, AM630 and SR144528. HU-210, CP55940, WIN55212-2 are cannabinoid receptor agonists with no or marginal $CB_1/CB_2$ selectivity. AM630 and SR144528 are both selective $CB_2$ receptor ligands and behave as inverse agonists rather than "silent" or "neutral" antagonists.

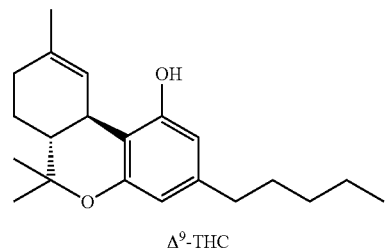

$\Delta^9$-THC

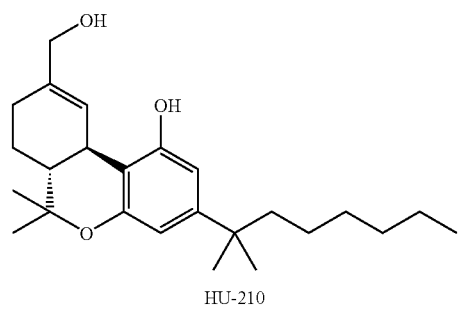

HU-210

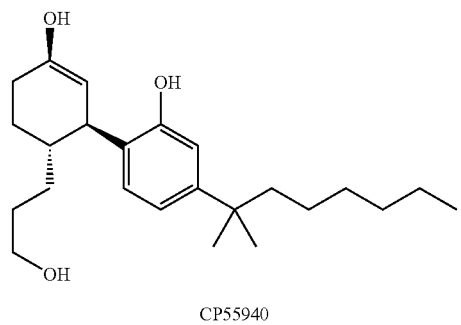

CP55940

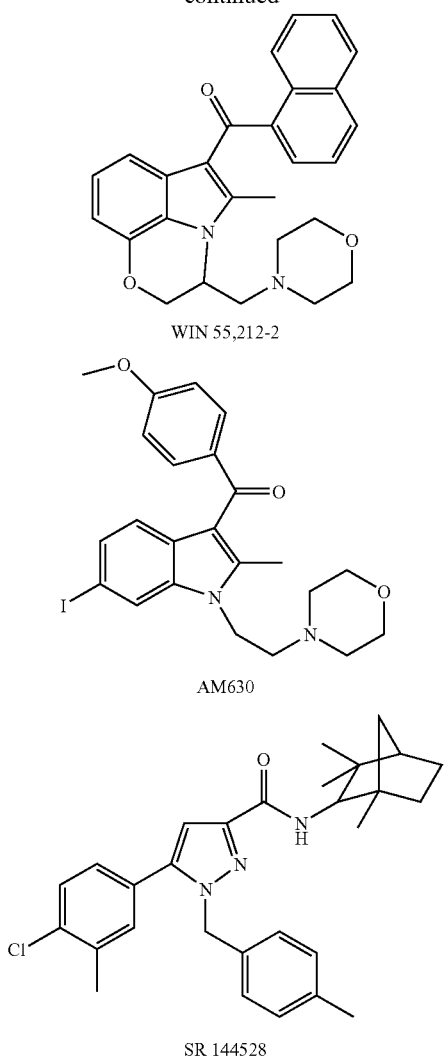

WIN 55,212-2

AM630

SR 144528

The $CB_2/CB_1$ affinity ratio is less for AM630 ($CB_2/CB_1$ affinity=165) than for SR144528 ($CB_2/CB_1$ affinity>700). Accordingly, SR144528 has been widely used as a pharmacological tool to determine $CB_2$ receptor-mediated effects. However, the use of SR144528 for $CB_2$ receptor-targeted imaging has never been tested directly since SR144528 is not conjugable. In other words, signaling moieties, such as fluorescent dyes, lanthanide chelates and nanoparticles, cannot be easily coupled to SR144528. Thus, to further study $CB_2$ receptor and diseases associated with an increase in the expression of this receptor, development of a conjugable SR144528 analog constitutes an essential step.

$CB_2$ receptor has become an attractive target for imaging and treating pain, inflammation, osteoporosis, diseases of the liver, growth of malignant gliomas and tumors of immune origin and immunological disorders such as multiple sclerosis. SR144528 is a selective CB2 receptor ligand with high CB2/CB1 affinity ratio (>700). Embodiments of the present invention couple moieties to a conjugable form of SR144528, to provide opportunities in $CB_2$ receptor targeted disease imaging and to screen for novel CB2 receptor ligands. Thus aspects of the present invention is a conjugable form of SR144528 with six carbon spacer ($C_6$SR144528 or mbc94) and, as one embodiment of the present invention, it is coupled to a near-infrared dye, IRDye™ 800CW NHS ester, for $CB_2$ receptor targeted imaging.

SUMMARY OF THE INVENTION

An aspect of the present invention is to synthesize a receptor or protein targeted agents for selective immune-related and cancer therapy. The chemistry is designed to be generally applicable to the application of targeted delivery of any conjugable moiety (therapeutic, imaging or combination). Preparation of small molecule ligand that is coupled to a drug, allows the drug to be selectively delivered and internalized into cells substantially improving cell kill and clinical efficacy.

Another aspect of the present invention is a conjugable selective $CB_2$ receptor ligand capable of targeted delivery.

Another aspect of the present invention is a method of targeted disease imaging and/or targeted disease treatment using a receptor ligand of the present invention.

Another aspect of the present invention is imaging a molecular event comprising administering a conjugate of the present invention.

Another aspect of the present invention is a method of treating and indication that is associated with CB2 expression by administering a conjugate of the present invention.

As stated above, another aspect of the present invention is a conjugable SR144528 analog, mbc94. This embodiment has a terminal amino group allowing easy conjugation to other molecules, including imaging moieties that can provide opportunities for $CB_2$ receptor targeted imaging.

In a related aspect, a near infrared (NIR) dye, IRDye™ 800CW NHS ester, labels mbc94 for optical imaging. The resulting imaging agent, NIRmbc94, was used to label $CB_2$ expressing cells.

Another aspect of the present invention is a method of imaging a molecular event in a sample, the method steps comprising administering to the sample a probe having an affinity for a target. The probe includes at least one of a $CB_2$ ligand/signaling agent conjugation. After the probe is administered, a signal from the probe may be detected. In embodiments of the present invention, the sample can be at least one of cells, tissue, cellular tissue, serum, cell extract, bodily fluids. The bodily fluids may be, for example, breast milk, sputum, vaginal fluids, urine.

Another aspect of the present invention is a method of quantifying the progression of a disease state progression that includes the steps of (a) administering to a first sample a conjugate that comprises a conjugable $CB_2$ receptor ligand and a signaling agent; (b) detecting a signal from the conjugate; (c) after a period of time from step (b), administering to a second sample a conjugate, (d) detecting a second signal; and (e) comparing the first signal with the second signal to determine the progress of a disease state. Again examples of the sample are at least one of cells, tissue, cellular tissue, serum, cell extract, bodily fluids.

Another aspect of the present invention is imaging a molecular event comprising administering a conjugate of the present invention.

Another aspect of the present invention is a method of treating cancer and immune cells comprising administering a conjugate of the present invention.

Another aspect of the present invention is a method of screening for $CB_2$ receptor ligands, including a) screening chemical libraries generated by combinatorial chemistry and b) ligands generated by rational design. The advantage of this screening assay is that it is performed on intact cells expressing CB2 receptors (example used here are the 2D4-DBT cells), thus preserving the intact pharmacodynamic characteristics of the CB2 receptor, as opposed to radioligand binding assays that are performed on cell homogenates and influence the pharmacodynamic characteristics of receptors. The screening assay can be performed as high-throughput, since it can be performed will cells seeded in 384 well plates and the fluorescent signal quantified by scanning (for example a Licor Odysee scanner when using NIR-mbc94).

wherein X is H or substituted with

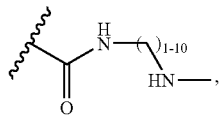

with at least X being substituted; and halo is fluorine, chlorine, bromine, iodine, and stereoisomers and conjugable analogs thereof, and an imaging agent or therapeutic agent binded thereto.

The conjugate may be of the following formula:

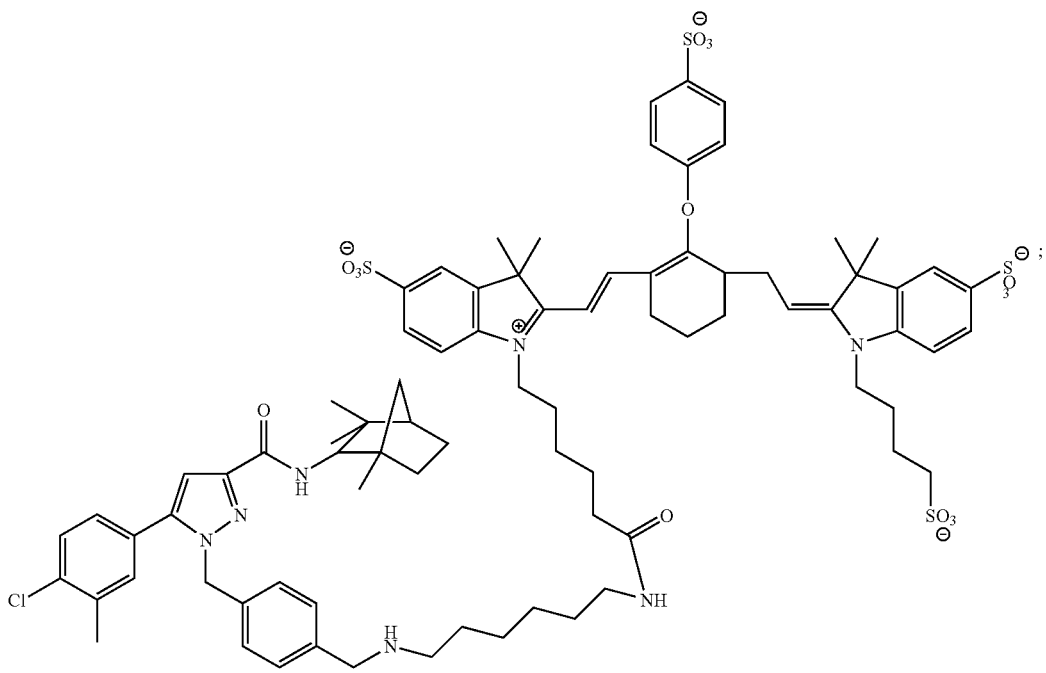

NIR-C$_6$SR144528

Thus, one embodiment of the present invention is a conjugate that includes a compound of the following formula:

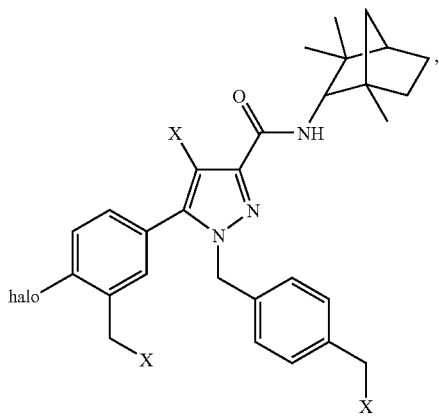

and stereoisomers thereof.

Example of the imaging agent include NIR dyes, and conjugable analogs thereof. Additionally, examples of the therapeutic agent (used interchangeably herein with the term drug) is etopiside or a conjugable analog thereof.

Another embodiment of the present invention is a method for delivering an agent to a sample of cells, comprising: (a) forming a conjugate of the present invention, and (b) introducing the conjugate to the sample. The agent is a signaling moiety or therapeutic agent/drug. The sample may be chosen from at least one of cells, tissue, cellular tissue, serum, cell extract, bodily fluids.

Another embodiment of the present invention is a method of imaging a molecular event in a sample that comprises: (a) administering to said sample a probe having an affinity for a target, the probe comprising a conjugate of the present invention and (b) detecting a signal from said probe.

This embodiment may further comprising the steps of (c) after a period of time from step (b), administering the probe to a second sample, (d) detecting a second signal; and (e) comparing the first signal with the second signal to determine the progress of a disease state.

Another embodiment of the present invention is a method of delivering a therapeutic agent to a targeted cell, that includes administering to a patient in need thereof a drug comprising conjugate of the present invention.

Another embodiment of the present invention are the compounds disclosed herein in a composition that includes a pharmaceutically acceptable carrier.

Many other embodiments and aspects will be obvious from a review of this disclosure and claims.

DESCRIPTION OF THE INVENTION

Embodiments of the present invention include compounds of the following formula:

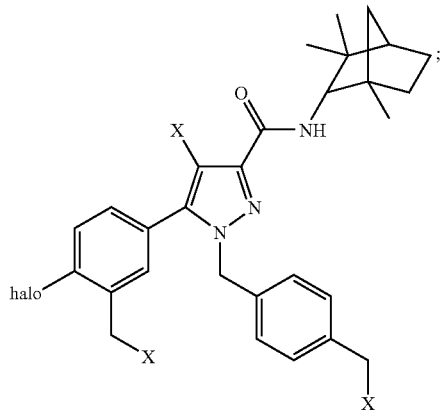

wherein X is H or substituted with

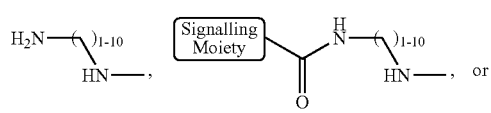

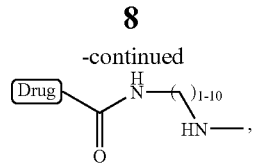

with at least one X being substituted; and halo is fluorine, chlorine, bromine, iodine;

and stereoisomers and conjugable analogs thereof.

Further embodiments of the present invention include the following compounds:

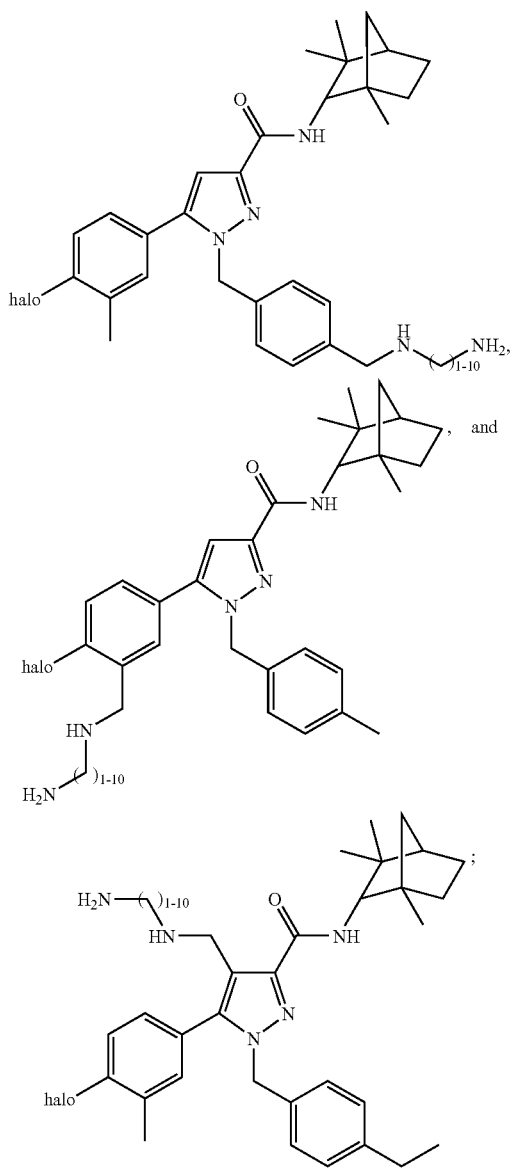

and analogs and conjugable forms thereof.

For the purposes of the present invention, the term analog encompasses isomers, homologs, or other compounds sufficiently resembling the base compound in terms of structure and do not destroy activity. "Conjugable forms," "conjugable compounds," and similar terms describe a form of the compound that can readily form a covalent form a covalent bond with a drug or a signaling agent such as an IR dye.

Also, for the purposes of the present invention, "halo" is fluorine, chlorine, bromine, iodine. In other embodiments of the present invention, halo is chlorine. The term "halo" or "halogen," as used herein, includes radio isotopes of halogen compounds, such as $I^{121}$ and $F^{19}$.

Examples include the following compounds:

Thus, other embodiments of the present invention include the following compounds:

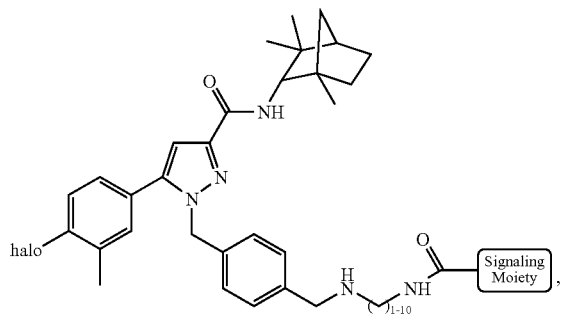

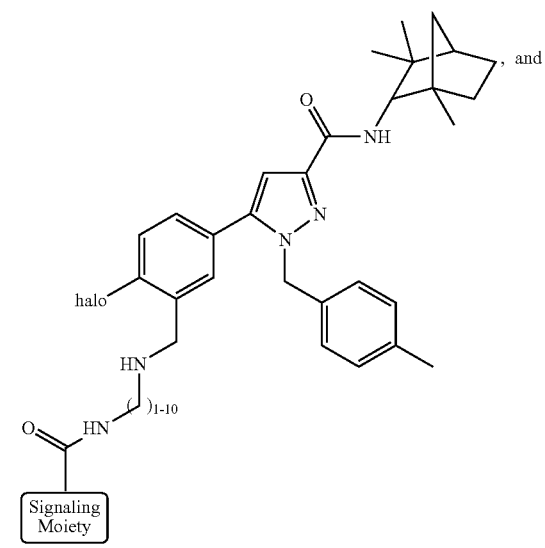

, and

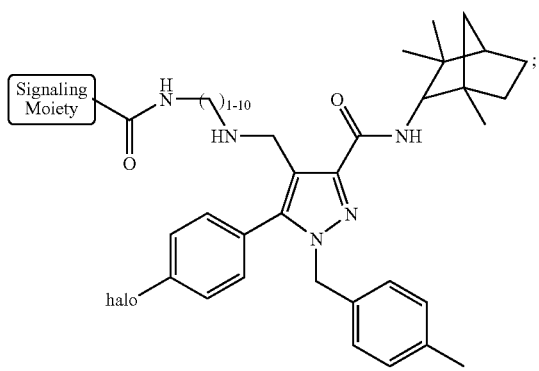

;

and analogs and conjugable forms thereof

The use of NIR (650-900 nm) light has gained increasing wide acceptance in molecular imaging during recent years in part because tissues are relatively transparent in this region of the electromagnetic spectrum, with hemoglobin, water and lipids exhibiting low absorption coefficients. Therefore, we labeled mbc94 with a NIR dye, IRDye™ 800CW NHS ester for NIR optical imaging. The reaction was monitored by HPLC. The resulting imaging agent, NIRmbc94, was used to label $CB_2$ expressing cells. Preliminary fluorescence imaging of live cells and competition study showed that indeed NIRmbc94 specifically labeled $CB_2$-expressing cells.

Figure 1:
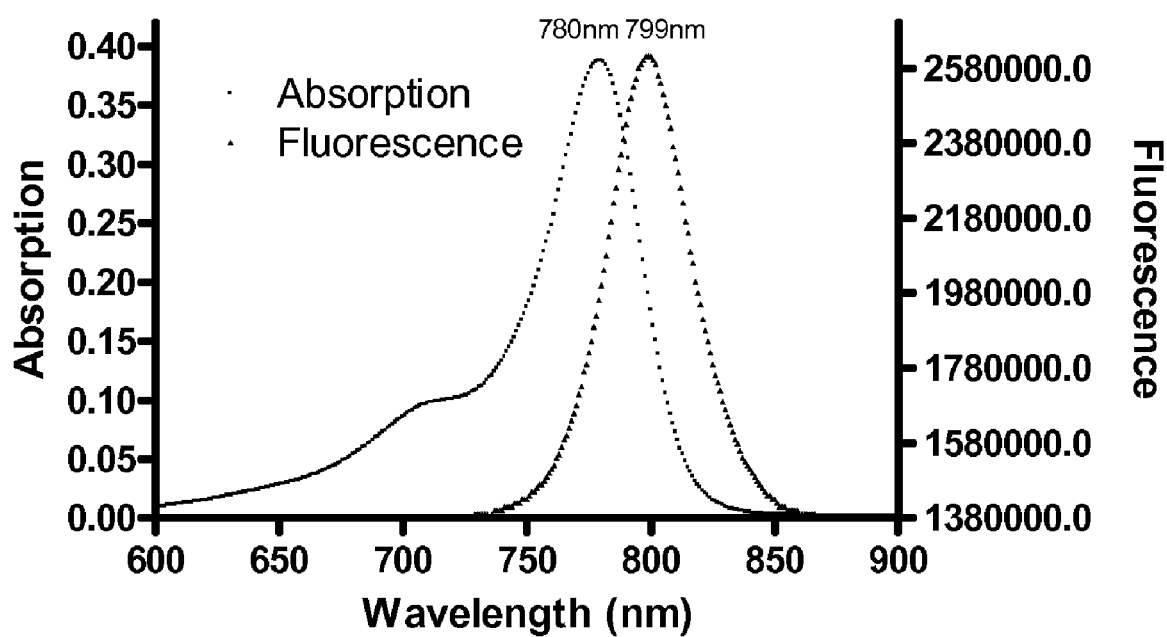
FIG. 1 is a graph that shows NIRmbc94 absorption and fluorescence.
Figure 2:
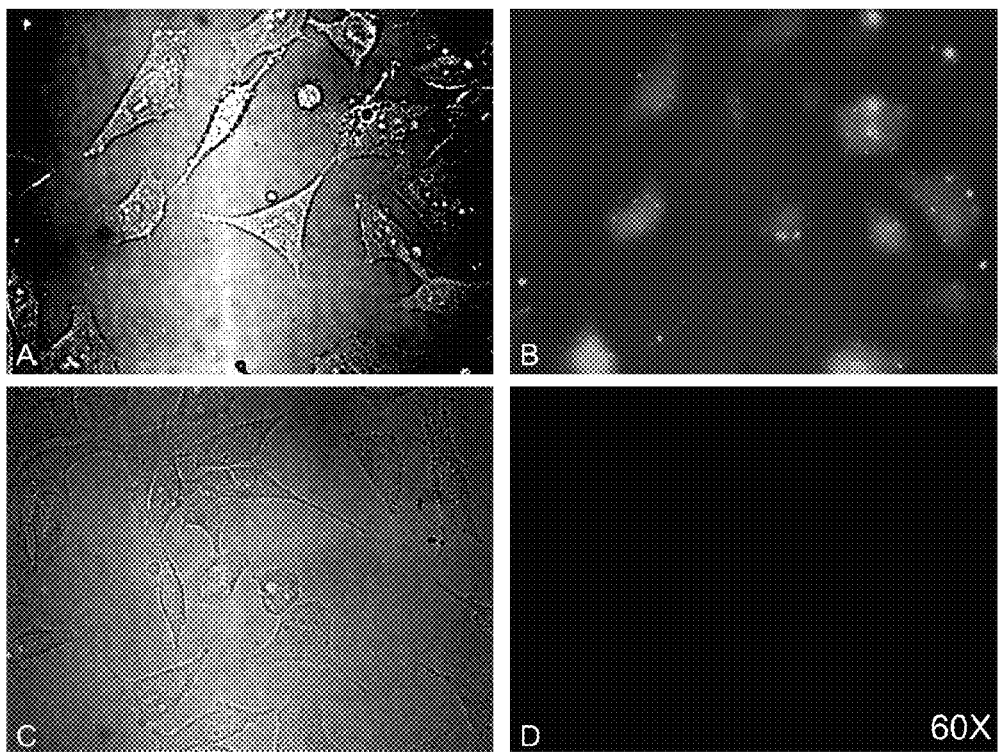
FIG. 2 shows fluorescence imaging of DBT cells incubated with NIRmbc94 or free NIR dye: (A) Phase contrast microscopy of cells dosed with NIRmbc94; (B) fluorescence imaging of cells dosed with 5 μM NIRmbc94; (C) Phase contrast microscopy of cells dosed with free NIR dye; (D) fluorescence imaging of cells dosed with 5 μM free NIR dye (control).
Figure 3:
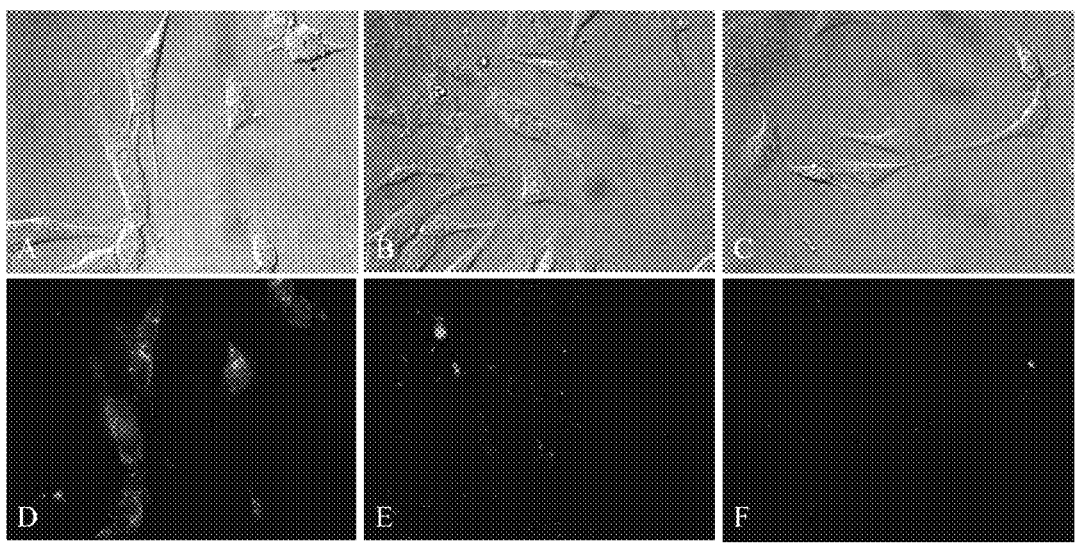
FIG. 3 shows fluorescence imaging of 2D4 ($CB_2$ expressing) and wild type (WT, non-$CB_2$ expressing) DBT cells: (A) phase contrast microscopy of 2D4 DBT cells dosed with 5 μM NIRmbc94; (B) phase contrast microscopy of WT DBT cells dosed with 5 μM NIRmbc94; (C) phase contrast microscopy of 2D4 DBT cells dosed with 5 μM NIRmbc94 and 100 nM SR144528; (D) fluorescence imaging of 2D4 DBT cells dosed with 5 μM NIRmbc94; (E) fluorescence imaging of WT DBT cells dosed with 5 μM NIRmbc94; (F) fluorescence imaging of 2D4 DBT cells dosed with 5 μM NIRmbc94 and 100 nM SR144528.

To test whether NIRmbc94 reliably binds to the $CB_2$ receptor, we already had in place a system wherein the receptor was both absent and present. Specifically, the highly malignant mouse astrocytoma cell line, DBT, lacks the targeted receptor (wild-type), and we generated a clone that stably expresses our target, 2D4-DBT (this data was confirmed by radioligand binding using [3H]-CP55940, yielding a Bmax of 2 pmol/mg). First we demonstrated that NIRmbc94 gave a significant signal (S/N=1.6) whereas the "free" dye (IRDye™ 800CW acid) does not produce significant fluorescence, as illustrated by microscopy in the NIR (thus indicating a lack of non-specific binding due to the dye: FIG. 2), Next, as a preliminary indicator of specific targeting of our receptor, both wild-type cells and 2D4 clones were incubated 5 µM concentration of NIRmbc94. FIG. 3 (B,E) shows that the fluorescence signal is relatively low in wild-type DBT cells compared to the clone (A,D).

A competition study gave further evidence for specific binding of NIRmbc94 to $CB_2$ receptors. Specifically, in a preliminary competitive binding experiment, the fluorescence signal was significantly reduced when 100 nM SR144528 was added to compete with 5 µM NIRmbc94 at the receptor site. The lack of fluorescence is due to the higher affinity unlabeled ligand, SR144528, (reference for affinity), occupying the receptor site and thus inhibiting binding by NIRmbc94. This preliminary pharmacological characterization is typical and the data indicate that we have indeed labeled our target of interest. More detailed pharmacological and biological characterization, including binding affinity ($K_d$) and reliable measurement of receptor expression ($B_{max}$) are in order and forthcoming.

Thus, embodiments of the present invention include conjugable $CB_2$ receptor ligand, mbc94, which has a terminal amino group, making it universally conjugable. A NIR dye labeled mbc94, NIRmbc94, specifically labeled $CB_2$-expressing DBT cells, whereas the same cells incubated with same concentration of free NIR dye did not show any significant signal. In addition, reduced fluorescence signal was observed from non-$CB_2$ expressing wild-type DBT cells incubated with NIRmbc94 compared to CB2-expressing DBT cells incubated with the same concentration of NIRmbc94. Finally, the specific binding of NIRmbc94 to $CB_2$ receptors was confirmed by in vitro competition study. A preliminary competition study in which cells were co-incubated with NIRmbc94 and SR144528 showed signal reduction compared to cells incubated with NIRmbc94 only. Overall, mbc94 constitutes a promising conjugable $CB_2$ receptor ligand. NIRmbc94 specifically binds to $CB_2$ receptors and can be potentially used to image $CB_2$-expressing cells in vivo, including immune and cancer cells.

Additional aspects of the present invention include the following compounds:
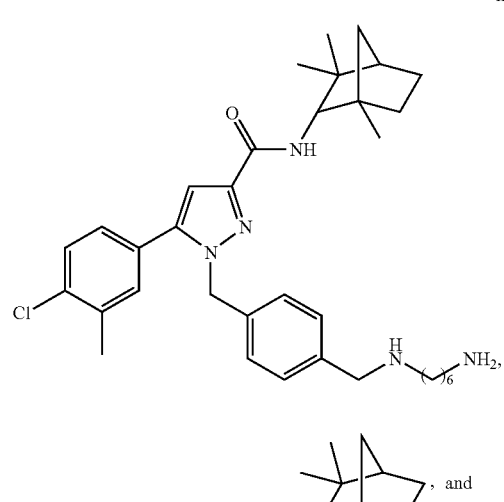
mbc94
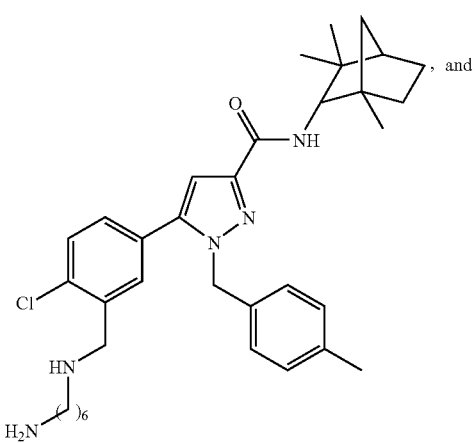
ES52
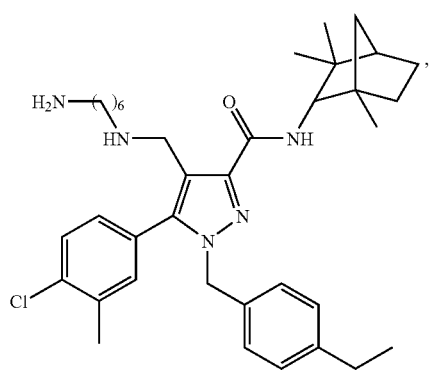
ES51
and analogs and conjugable forms thereof
The above compounds may be made as follows:
Scheme 1. Synthesis of the conjugable compound 6$^a$
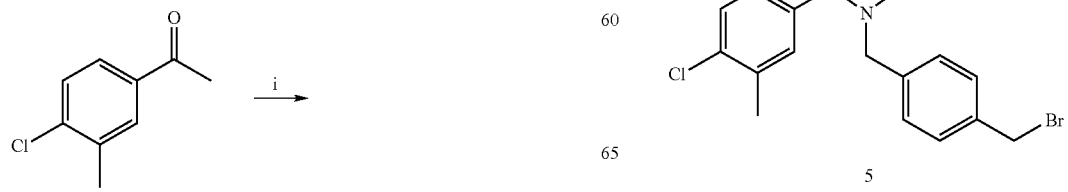
-continued
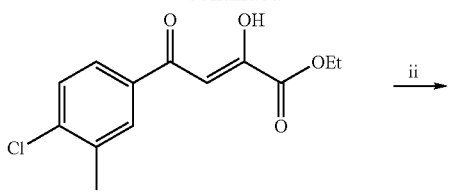
1
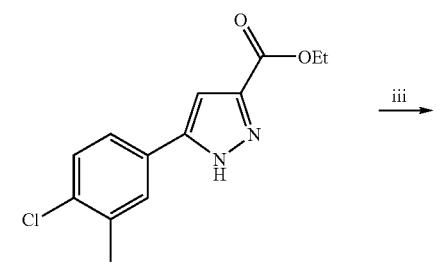
2
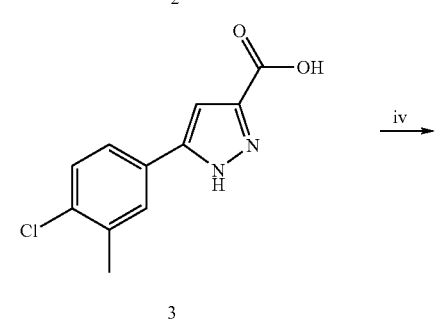
3
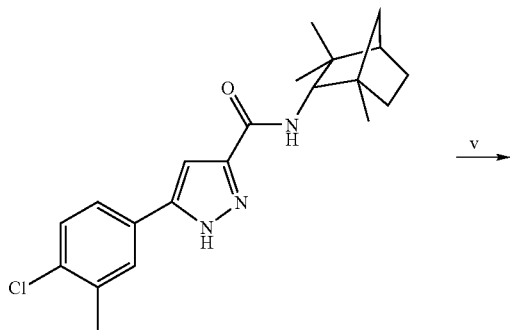
4
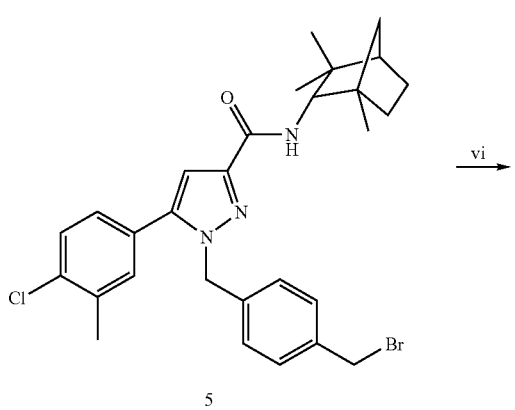
5

13
-continued
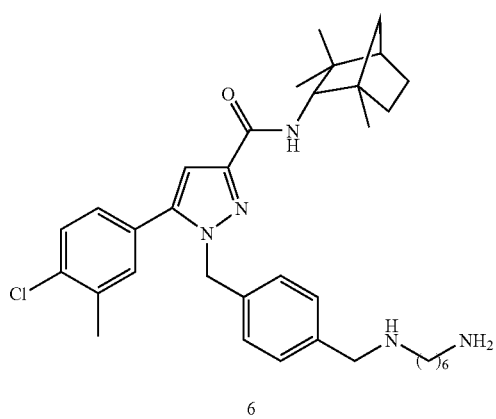
6
[a]Reagents and conditions: (i) Diethyl oxalate, EtONa, EtOH, atm N$_2$, reflux, 95%; (ii) Hydrazine hydrate, EtOH, atm N$_2$, reflux, 98%; (iii) NaOH, EtOH/H$_2$O (v/v), reflux, 86%; (iv) Fenchylamine, HBTU, TEA, CH$_2$Cl$_2$/DMF, atm N$_2$, rt, 79%; (v) α,α'-Dibromo-p-xylene, NaH, dry toluene, atm N$_2$, reflux, 67%; (vi) 1,6-Hexanediamine, dry CH$_2$Cl$_2$, atm N$_2$, rt, 69%.
Scheme 2. Synthesis of the conjugable compound 14[a]
14
-continued
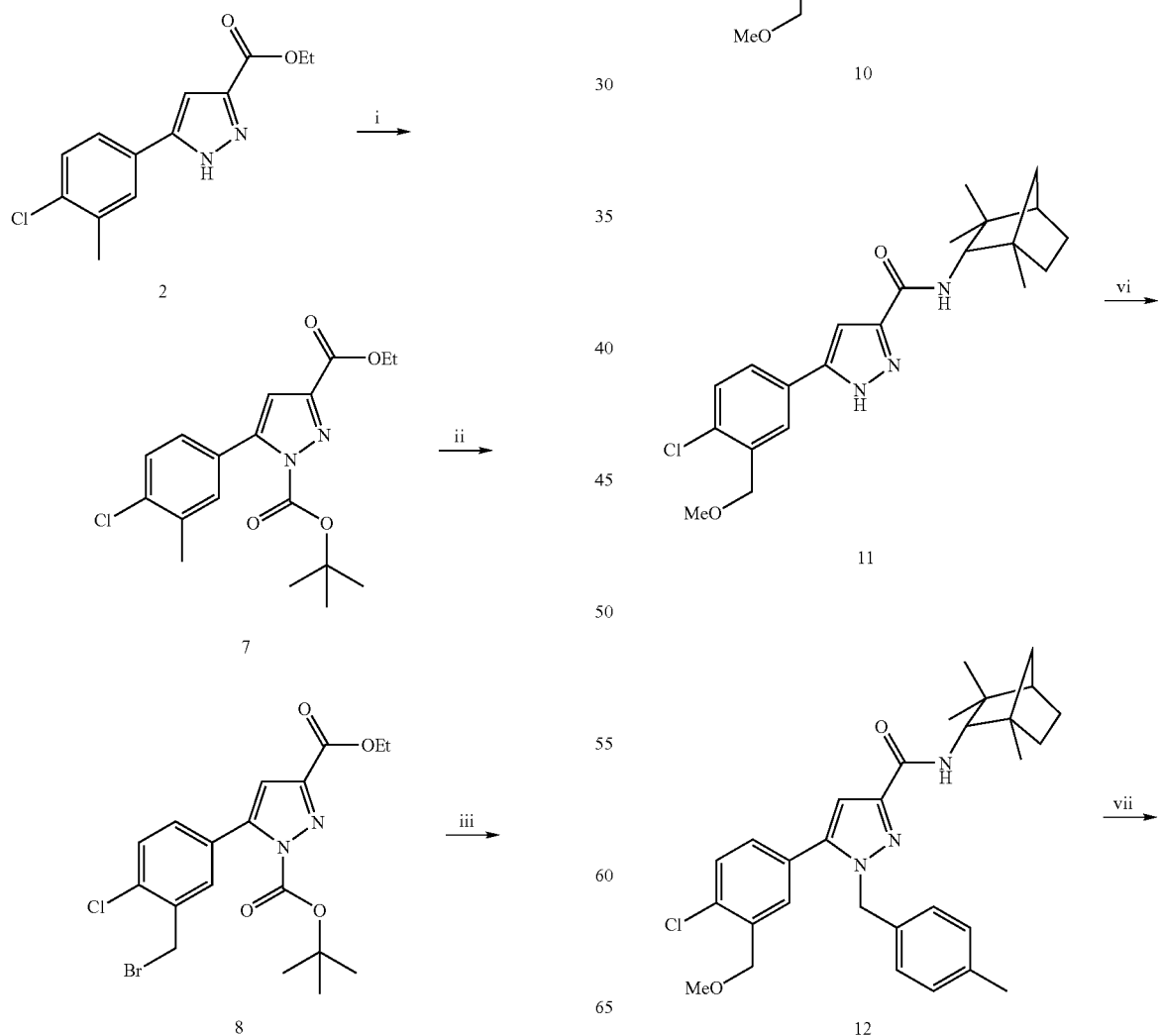

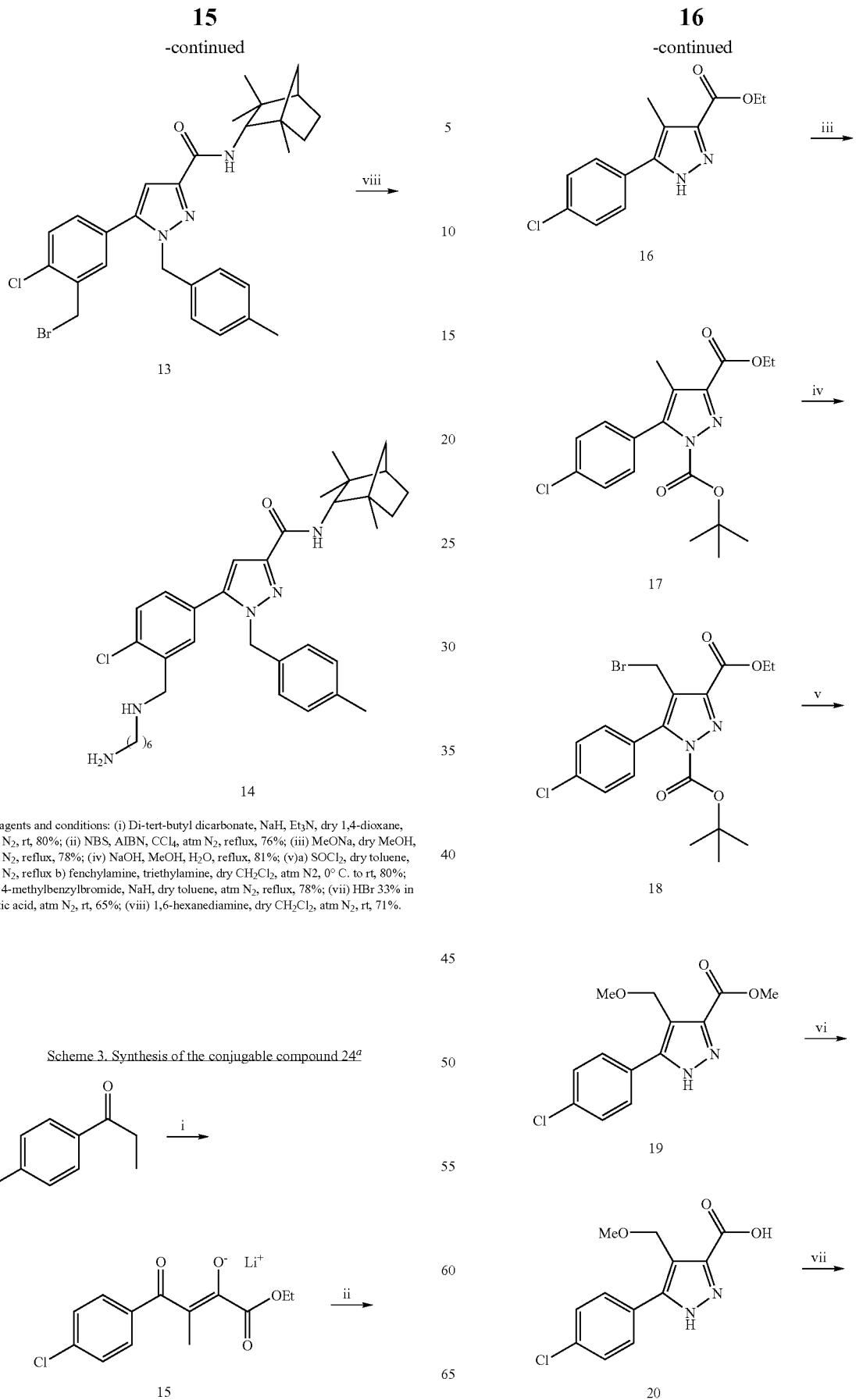

*Reagents and conditions: (i) Di-tert-butyl dicarbonate, NaH, Et$_3$N, dry 1,4-dioxane, atm N$_2$, rt, 80%; (ii) NBS, AIBN, CCl$_4$, atm N$_2$, reflux, 76%; (iii) MeONa, dry MeOH, atm N$_2$, reflux, 78%; (iv) NaOH, MeOH, H$_2$O, reflux, 81%; (v)a) SOCl$_2$, dry toluene, atm N$_2$, reflux b) fenchylamine, triethylamine, dry CH$_2$Cl$_2$, atm N2, 0° C. to rt, 80%; (vi) 4-methylbenzylbromide, NaH, dry toluene, atm N$_2$, reflux, 78%; (vii) HBr 33% in acetic acid, atm N$_2$, rt, 65%; (viii) 1,6-hexanediamine, dry CH$_2$Cl$_2$, atm N$_2$, rt, 71%.

Scheme 3. Synthesis of the conjugable compound 24$^a$

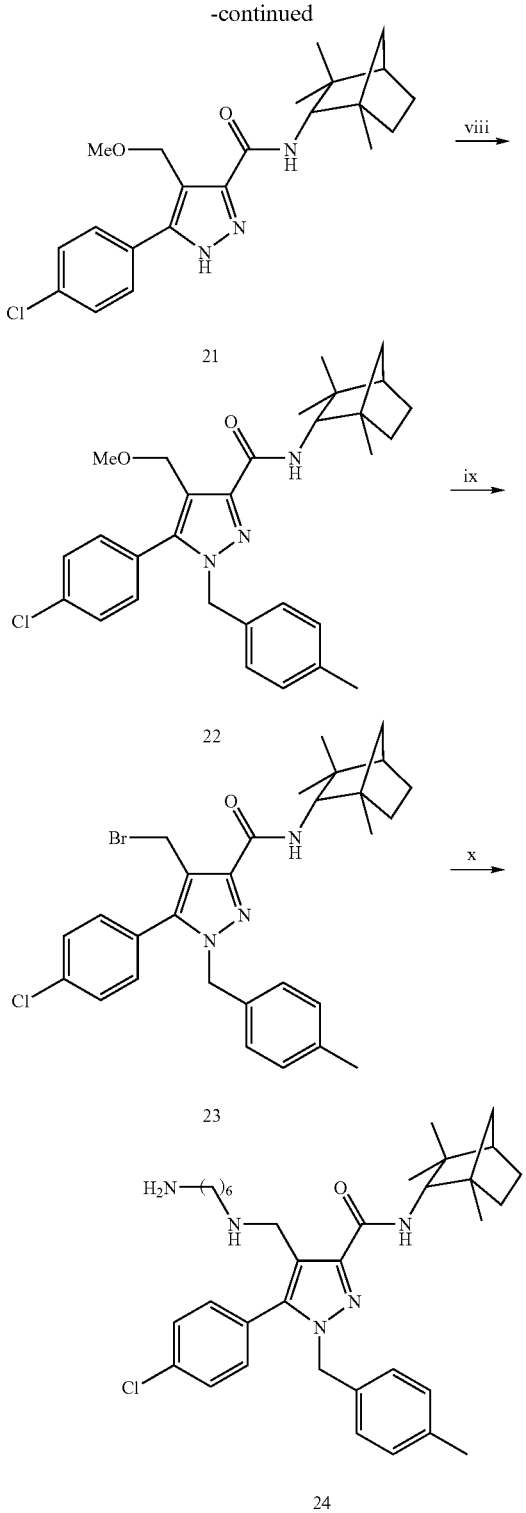

*Reagents and conditions: (i) Lithium bis(trimethylsily)amide 1.0 M in THF, diethyl oxalate, dry THF, dry cyclohexane, atm N$_2$, rt, 71%; (ii) Hydrazine monohydrate, glacial acetic acid, reflux, 82%; (iii) Di-tert-butyl dicarbonate, NaH, Et$_3$N, dry 1,4-dioxane, atm N$_2$, rt, 81%; (iv) NBS, AIBN, CCl$_4$, atm N$_2$, reflux, 72%; (v) MeONa, dry MeOH, atm N$_2$, reflux, 62%; (vi) NaOH, MeOH, H$_2$O, reflux, 90%; (vii) a) SOCl$_2$, dry toluene, atm N$_2$, reflux; b) fenchylamine, triethylamine, dry CH$_2$Cl$_2$, atm N$_2$, 0° C. to rt, 75%; (viii) 4-methylbenzylbromide, NaH, dry toluene, atm N$_2$, reflux, 68%; (ix) HBr 33% in acetic acid, atm N$_2$, rt, 90%; (x) 1,6-hexanediamine, dry CH$_2$Cl$_2$, atm N$_2$, rt, 80%.

In the above schemes, compound 6 was obtained by reaction of 1,6-diaminohexane with the key brominated intermediate 5. See Bai, M.; Sexton, M.; Stella, N.; Bornhop, D. J. "MBC94, a conjugable Ligand for cannabinoid CB$_2$ receptor imaging" *Bioconjugate Chem.* 2008, 19, 988-992.

This compound 5 was obtained starting with 4'-chloro-3'-methylacetophenone and diethyloxalate. 4'-Chloro-3'-methylacetophenone was added, over basic conditions, on the diethyloxalate, to give the intermediate 1, which was converted into the desired 1-H-pyrazole-3-carboxylic acid ethyl ester 2 using hydrazine monohydrate. See Pommery, N.; Taverne, T.; Telliez, A.; Goossens, L.; Charlier, C.; Pommery, J.; Goossens, J.-F.; Houssin, R.; Durant, F.; Hénichart, J.-P. "New COX-2/5-LOX inhibitors: apoptosis-inducing agents potentially useful in prostate cancer chemotherapy" *J. Med. Chem.* 2004, 47, 6195-6206. Also see Seltzman, H. H.; Foster, M. C.; Wyrick, C. D.; Burgess, J. P.; Carroll, F. I. "Tritiation of the cannabinoid receptor antagonist SR144528 involving lithium aluminum tritide reduction; assessment of the kinetic isotope effect by $^3$H-NMR" *J. Label. Compd. Radiopharm.* 2005, 48, 589-596.

Alkaline hydrolysis of the ethylic ester yielded to the corresponding carboxylic acid 3, which was coupled to fenchylamine using HBTU to afford the amide 4. Benzylation of the pyrazole moiety was next performed using a large excess of α,α'-dibromo-p-xylene in the presence of sodium hydride. See Suchocki, J. A.; May, E. L.; Martin, T. J.; George, C.; Martin, B. R. "Synthesis of 2-exo- and 2-endo-mecamylamine analogues. Structure-activity relationships for nicotinic antagonism in the central nervous system" *J. Med. Chem.* 1991, 34, 1003-1010.

The resulting benzyl bromide derivative 5 was then treated with 1,6-diaminohexane to give the desired conjugable compound 6.

The first step of the synthesis of the conjugable compound 14 was the introduction of tert-butyloxycarbonyl (Boc) protective group on the N-1 position of intermediate 2's pyrazole moiety. This protection was carried out using di-tert-butyldicarbonate in the presence of sodium hydride and triethylamine. See Bart, F.; Casellas, P.; Millan, J.; Oustric, D.; Rinaldi, M.; Sarran, M. "3-Pyrazolecarboxamide derivatives having cannabinoid receptor affinity" 1999, US005925768A.

Bromination of N-Boc intermediate 7 was performed under classical conditions, using N-bromosuccinimide (NBS) in the presence of 2,2'-azobis(2-methylpropionitrile) (AIBN) to furnish the brominated compound 8. Refluxing 8 in anhydrous methanol and in the presence of sodium methoxide resulted in both conversion of the bromomethyl into a methoxymethyl and N-deprotection of the pyrazole moiety. Note that using these experimental conditions a trans-esterification reaction was also observed, as compound 9 was isolated as a methyl ester. Saponification of 9 furnished the corresponding carboxylic acid 10, which was activated as an acyl chloride and treated with fenchylamine to give the amide 11, immediately followed by the benzylation of the pyrazole ring using 4-methylbenzyl bromide. The key step in this synthetic pathway was the regeneration of the bromomethyl function from the methoxymethyl group of 12. This reaction was achieved by action of hydrobromide acid (33% in acetic acid) at room temperature. Walker, J. R.; Alshafie, G.; Nieves, N.; Ahrens, J.; Clagett-Dame, M.; Abou-Issa, H.; Curley Jr., R. W. "Synthesis and preliminary chemotherapeutic evaluation of the fully C-linked glucuronide of N-(4-hydroxyphenyl)retinamide" *Bioorg. Med. Chem.* 2006, 14, 3038-3048, and Katz, H. E. "Chelate and macrocycle effects in the 2,2'-bipyridine N,N-dioxide complexation of alkyltin trichlorides" *J. Org. Chem.* 1985, 50, 2086-2091.

The resulting benzyl bromide derivative 13 was then treated with 1,6-diaminohexane to give the desired conjugable compound 14.

The synthesis of conjugable 24 was achieved using a synthetic approach similar to that one used for the preparation of 14. In the first step of the synthesis, the 4'-chloropropiophenone was added to diethyloxalate in the presence of hexamethyldisilazane lithium salt furnishing the pyrazole moiety's precursor 15 as a lithium salt. 15 was cyclized by action of hydrazine to afford the 4-methylpyrazole scaffold (16). As previously described for the synthesis of 14, compound 16 was then N-protected using a Boc group (17), followed by a free radical bromination (18), and a concomitant N-deprotection, methoxylation and trans-esterification furnishing intermediate 19. 19 was next saponified under basic conditions to afford the carboxylic acid 20, which was amidified (21) and then benzylated using 4-methylbenzyl bromide (22). 22 was treated by hydrobromic acid (33% in acetic acid) to afford bromide derivative 23. Conjugable derivative 24 was finally obtained by addition of 1,6-diaminohexane on 24.

Thus, other embodiments of the present invention include the following compounds:

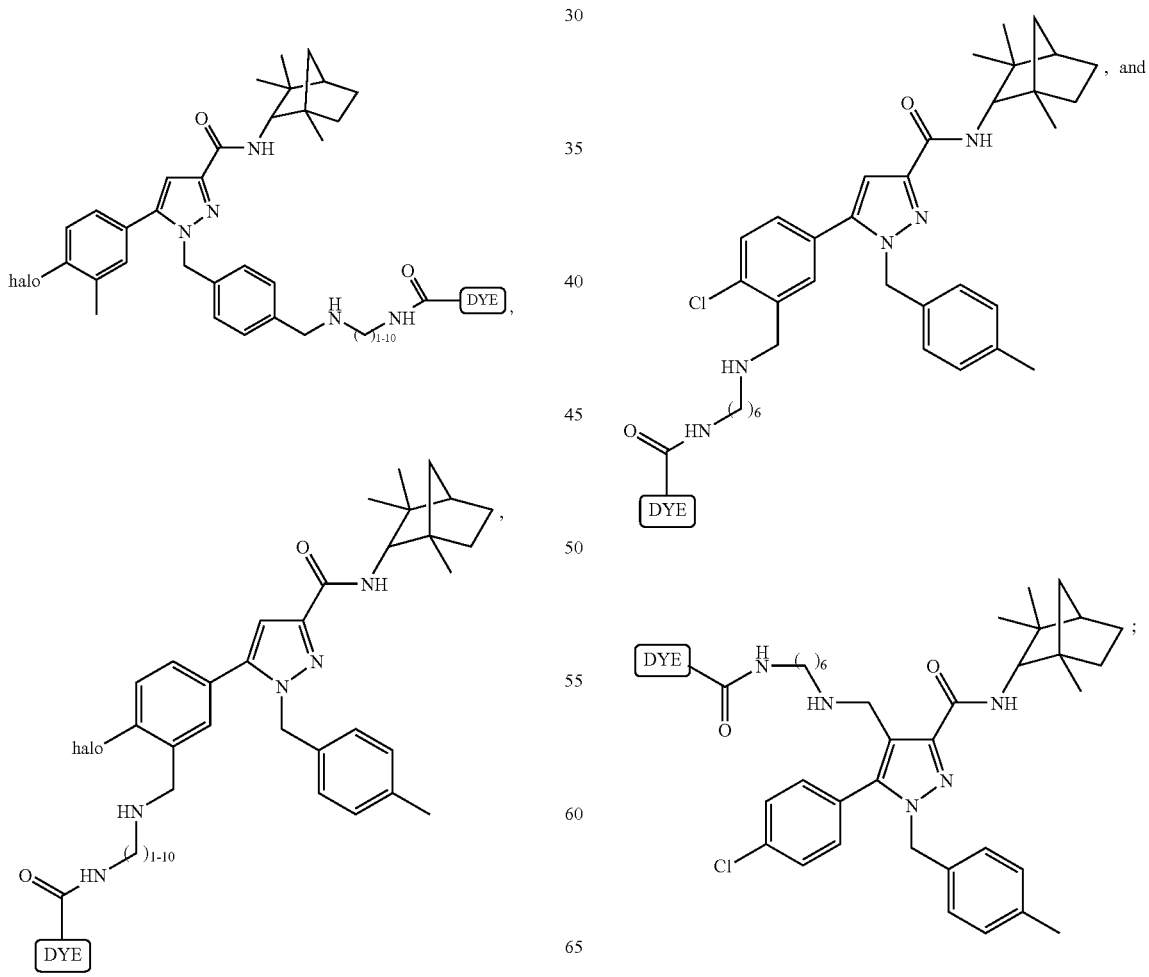

and stereoisomers and conjugable forms thereof

Aspects of the invention related to imaging are carried out as described in Bornhop et al., US Application Publication Number 20060147379, incorporated herein by reference.

Two fluorescent dyes, IRDye™ 800CW NHS ester (LI-COR Biosciences, ϵ=300,000 L/mol cm in methanol) and Lissamine™ rhodamine B sulphonyl chloride (Invitrogen, ϵ=300,000 L/mol cm in methanol) are examples of signaling parts to conjugate of the present invention.

Also includes are dyes, such as, for example, near-infrared fluorophores/fluorescent dyes. Examples include cyanine dyes which have been used to label various biomolecules. See U.S. Pat. No. 5,268,486, which discloses fluorescent arylsulfonated cyanine dyes having large extinction coefficients and quantum yields for the purpose of detection and quantification of labeled components.

Additional examples include compounds of the following formulas:

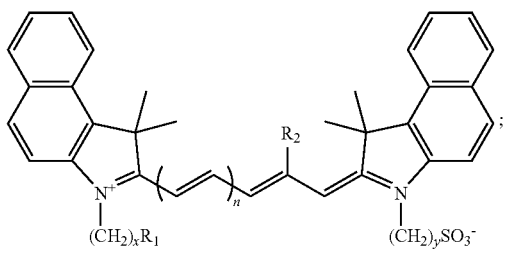

General Cyanine dye

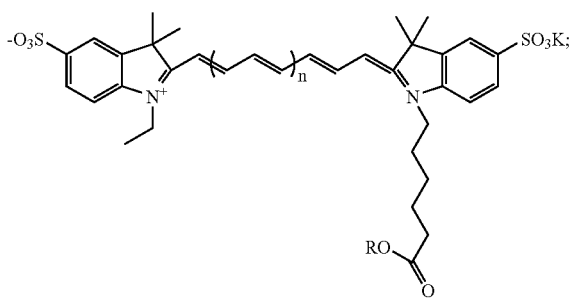

CY-Family of dyes and analogs thereof.

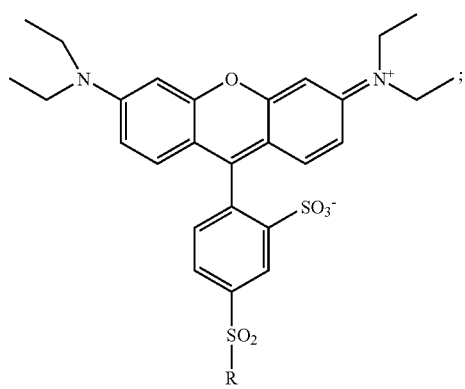

Lissamine-Rhodamine abs/em = 560nm, 590nm

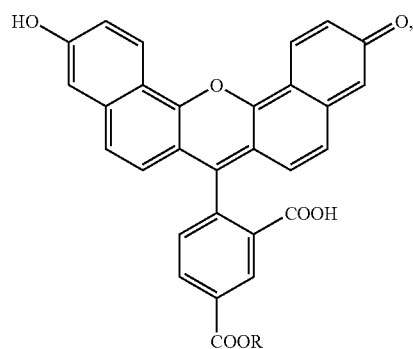

Carboxynaphthofluorescein abs/em = 580nm, 690nm

Additional examples include dyes disclosed in U.S. patent application Ser. No. 11/267,643, incorporated herein by reference, are dyes of the present invention. Additionally, dyes of U.S. Pat. No. 6,995,274, incorporated herein by reference, are dyes of the present invention.

Accordingly, the following dye is a specific example:

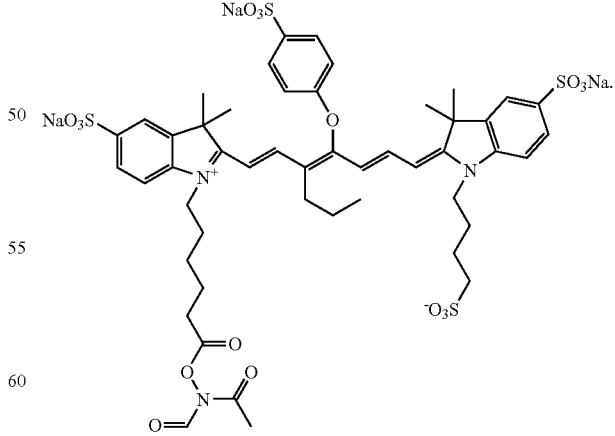

U.S. Pat. No. 6,995,274 additionally discloses the following dyes, all of which, when joined with a probe, are embodiments of the present invention:

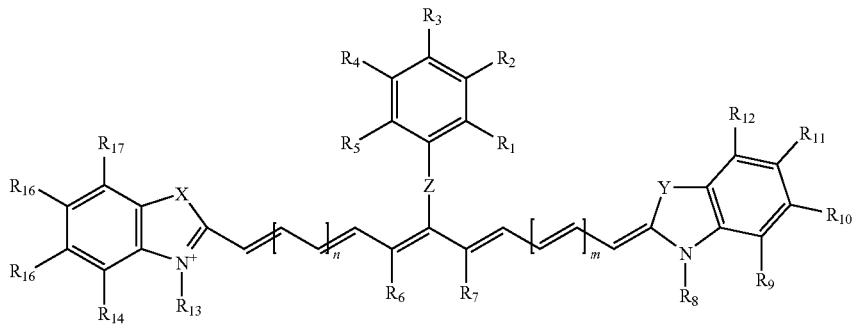

wherein, Z is a heteroatom having at least one lone pair of electrons. In one embodiment, Z is O, S, or $NR_{35}$, wherein $R_{35}$ is H or alkyl. In embodiments, Z is of such a structure that only one atom is in the direct linkage between the benzene ring bonded to Z and to the polyene chain of:

bonded to Z. Side chains on the linkage between the benzene ring and the polyene chain are acceptable. In those embodiments having side chains, lower alkyl side chains may be used.

$R_1$-$R_5$ are each independently H, alkyl, halo, carboxyl, amino, or $SO_3$—$Cat^+$, wherein $Cat^+$ is a cation and at least one of $R_1$-$R_5$ is $SO_3$—$Cat^+$. In embodiments, $R_3$ is $SO_3$—$Cat^+$. In other embodiments, $Cat^+$ is $H^+$ or an alkali metal ion such as $Na^+$.

$R_6$ and $R_7$ are each H, alkyl, or optionally, together with the

group to which they are bonded, form a ring. In embodiments, $R_6$ and $R_7$ together with the atoms to which they are bonded form a ring. These rings may have 4 to 10 member atoms, more preferably 5 or 6 member atoms. In one embodiment, the ring including $R_6$ and $R_7$ is substituted, with, for example, a sulfonato radical.

The integers m and n are each independently integers from 0 to 5. In embodiments, both the sum of m and n is two. Additionally, the sum of m and n may be one. In other embodiments, both m and n are zero. As the sum of m and n rises, so too does the wavelength of the dye. Generally, the addition of each double bond in the polyene chain can increase the wavelength by about 40 to 120 nm. For the absorption changes accompanied with trimethine to pentamethine or pentamethine to heptamethine, there is a typically a bathochromic shift (red shift) of about 100 nm. For example, when m and n are both 0, the wavelength of the preferred dye is about 770 nm. When m and n are both 1, the wavelength of the preferred dye is about 950 nm. The most preferred dyes operate in the NIR spectrum (600-1000 nm).

X and Y are each independently O, S, Se, or $CR_{19}R_{20}$, wherein $R_{19}$ and $R_{20}$ are each independently alkyl, or optionally form a ring together with the carbon atom to which they are bonded. In embodiments, X and Y are a heteroatom such as O, S, and Se. When X or Y is $CR_{19}R_{20}$, both $R_{19}$ and $R_{20}$ may be both lower alkyl, including methyl.

$R_8$ and $R_{13}$ are each independently alkyl, $(CH_2)_rR_{25}$ or $(CH_2)_rR_{18}$; wherein at least one of $R_8$ and $R_{13}$ is $(CH_2)_rR_{18}$ and wherein r is an integer from 1 to 50, and $R_{25}$ is a functional group that does not directly react with a carboxyl, hydroxyl, amino, or a thiol group, and $R_{18}$ is a functional group that can react with a carboxyl, hydroxyl, amino, or thiol group. In one embodiment, one of $R_8$ and $R_{13}$ is $(CH_2)_rR_{18}$ and the other is $(CH_2)_nR_{25}$. In other words, one of $R_8$ and $R_{13}$ reacts with a biomolecule to form a bond to that biomolecule, and that the other does not react. The $R_{18}$ group must be able to covalently bond with the biomolecule being labeled. $R_{18}$ groups include mercapto, carboxyl, amino, haloalkyl, phosphoramidityl, N-hydroxy succinimidyl ester, sulfo N-hydroxy succinimidyl ester, isothiocyanato, iodoacetamidyl, and maleimidyl. $R_{25}$ groups include hydroxyl, thioacetyl, and sulfonato.

$R_9$-$R_{12}$ and $R_{14}$-$R_{17}$ are each independently H, alkyl, halo, amino, sulfonato, $R_{21}COOH$, $R_{21}OR_{22}$, $R_{21}SR_{22}$, or $R_{21}COOR_{22}$ wherein $R_2$, is a bond or alkylene and $R_{22}$ is alkyl, or optionally $R_{11}$ and $R_{12}$ together with the atoms to which they are bonded form an aromatic ring, or optionally $R_{16}$ and $R_{17}$ together with the atoms to which they are bonded form an aromatic ring. In one embodiment, one or both of $R_{11}$ and $R_{16}$ is sulfonato. In another embodiment, when $R_{11}$ and $R_{12}$ together with the atoms to which they are bonded form an aromatic ring, the ring is substituted in at least one position with a sulfonato group. In another embodiment, when $R_{16}$ and $R_{17}$ together with the atoms to which they are bonded form an aromatic ring, the ring is substituted in at least one position with a sulfonato group, a halo group, an alkyl substituent, or an amino substituent.

Another cyanine dye that can be used with the present invention is of the following formula:

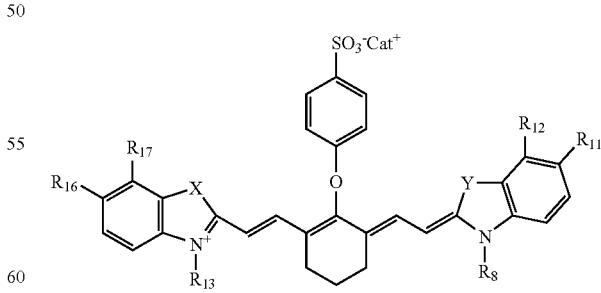

$Cat^+$ is a cation. In embodiments, $Cat^+$ is $H^+$ or a metal ion. More preferably, $Cat^+$ is an alkali metal ion, most preferably $Na^+$. X and Y are each independently O, S, Se, or $(CH_3)_2C$.

$R_8$ and $R_{13}$ are each independently alkyl, $(CH_2)_rR_{25}$ or $(CH_2)_rR_{19}$; wherein at least one of $R_8$ and $R_{13}$ is $(CH_2)_rR_{18}$ and wherein r is an integer from 1 to 50, and $R_{25}$ is a functional group that does not directly react with a carboxyl, hydroxyl, amino, or a thiol group, and $R_{18}$ is a functional group that can react with a carboxyl, hydroxyl, amino, or thiol group. In one embodiment, one of $R_8$ and $R_{13}$ is $(CH_2)_r R_{18}$ and the other is $(CH_2)_n R_{25}$. In other words, one of $R_8$ and $R_{13}$ reacts with a biomolecule to form a bond to that biomolecule, and that the other does not react. The $R_{18}$ group must be able to covalently bond with the biomolecule being labeled. $R_{18}$ groups include mercapto, carboxyl, amino, haloalkyl, phosphoramidityl, N-hydroxy succinimidyl ester, sulfo N-hydroxy succinimidyl ester, isothiocyanato, iodoacetamidyl, and maleimidyl. $R_{25}$ groups include hydroxyl, thioacetyl, and sulfonato.

$R_{11}$ and $R_{12}$ are either H, sulfonato, or together with the atoms to which they are bonded form an aromatic ring. In a preferred embodiment, $R_{11}$ is sulfonato. In another preferred embodiment, when $R_{11}$ and $R_{12}$ together with the atoms to which they are bonded form an aromatic ring, the ring is substituted in at least one position with a sulfonato group.

$R_{16}$ and $R_{17}$ are either H, sulfonato, or together with the atoms to which they are bonded form an aromatic ring. In a preferred embodiment, $R_{16}$ is sulfonato. In another preferred embodiment, when $R_{16}$ and $R_{17}$ together with the atoms to which they are bonded form an aromatic ring, the ring is substituted in at least one position with a sulfonato group.

Further examples of cyanine dyes that can be used in connection with the present invention are those cyanine dyes that can be excited efficiently by commercially available equipment purchasable through companies such as Toshiba, Phillips, Blue Sky Research, and NEC.

Examples of how the above cyanine dyes may be prepared are shown in US 2004/0014981. That is, the cyanine dyes disclosed herein are prepared using methods that are well known in the art. Generally, cyanine dyes are prepared according to the procedures taught in Hamer, F. M., Cyanine Dyes and Related Compounds, Weissberger, M. A., ed. Wiley Interscience, N.Y. 1964. Further, U.S. Pat. Nos. 4,337,063; 4,404,289 and 4,405,711, incorporated herein by reference, describe a synthesis for a variety of cyanine dyes having N-hydroxysuccinimide active ester groups. U.S. Pat. No. 4,981,977, incorporated herein by reference, describes a synthesis for cyanine dyes having carboxylic acid groups. U.S. Pat. No. 5,268,486, incorporated herein by reference, discloses a method for making arylsulfonate cyanine dyes. U.S. Pat. No. 6,027,709, discussed below, and incorporated herein by reference, discloses methods for making cyanine dyes having phosphoramidite groups. U.S. Pat. No. 6,048,982, incorporated herein by reference, discloses methods for making cyanine dyes having a reactive group selected from the group consisting of isothiocyanate, isocyanate, phosphoramidite, monochlorotriazine, dichlorotriazine, mono- or di-halogen substituted pyridine, mono- or di-halogen substituted diazine, aziridine, sulfonyl halide, acid halide, hydroxysuccinimide ester, hydroxy sulfosuccinimide ester, imido ester, glyoxal and aldehyde.

Additional dyes that can be used with the present invention are the following:

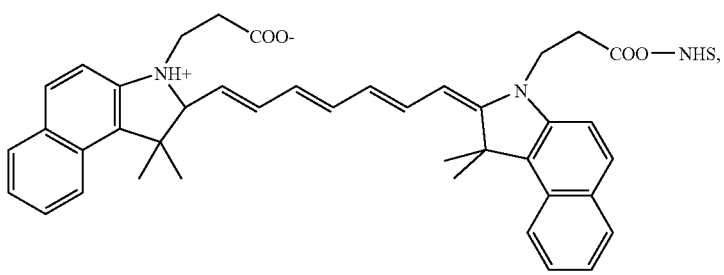

Cypate NHS-Achilefu

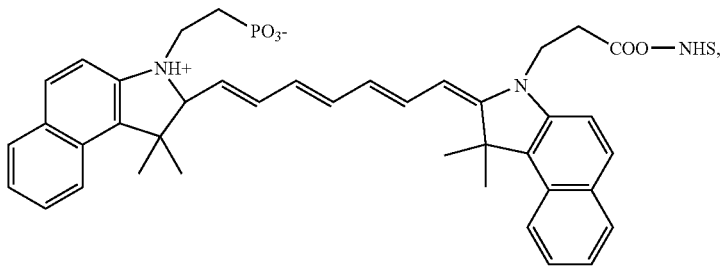

CY5.5-Amersham, Invitrogen

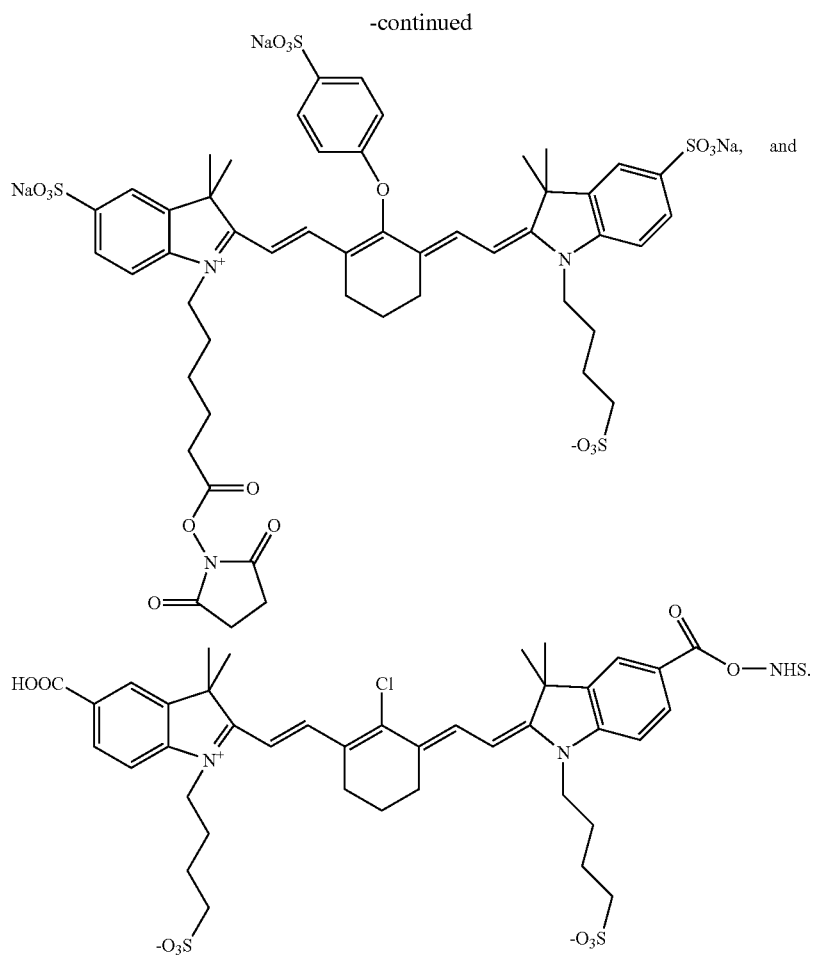

NIR-820 Pham, Tung et al.

Even further examples include the dyes disclosed in U.S. Pat. No. 6,027,709.

U.S. '709 discloses dyes which have the following general formula:

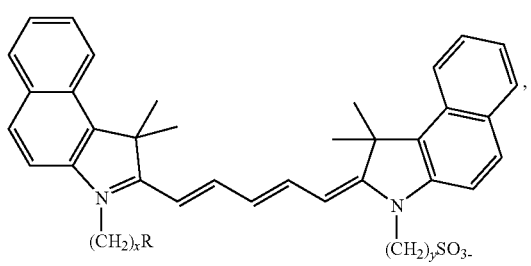

wherein R is —OH, —CO$_2$H, —NH$_2$, or —NCS and each of x and y, independently, is an integer selected from 1 to about 10. In preferred embodiments, each of x and y, independently, is an integer between about 2 and 6.

In one embodiment, the dye is N-(6-hydroxyhexyl)N'-(4-sulfonatobutyl)-3,3,3',3'-tetramethylbenz(e)indodicarbocyanine, which has the formula:

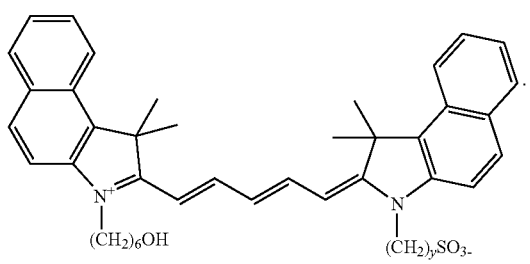

In a second embodiment, the dye is N-(5-carboxypentyl) N'-(4-sulfonatobutyl)3,3,3',3'-tetramethylbenz(e)indodicarbocyanine, which has the formula:

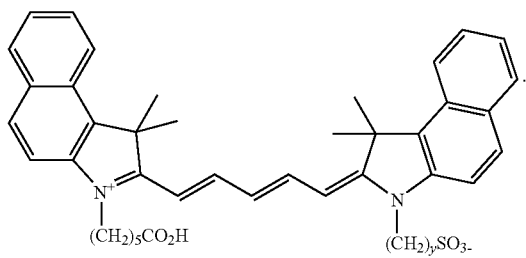

These two dyes are embodiments because they have commercially available precursors for the linking groups: 6-bromohexanol, 6-bromohexanoic acid and 1,4-butane sultone (all available from Aldrich Chemical Co., Milwaukee, Wis.). The linking groups provide adequate distance between the dye and the biomolecule for efficient attachment without imparting excessive hydrophobicity. The resulting labeled biomolecules retain their solubility in water and are well-accepted by enzymes.

These dyes, wherein R is —$CO_2H$ or —OH can be synthesized, as set forth in detail in the U.S. '709 patent, by reacting the appropriate N-(carboxyalkyl)- or N-(hydroxyalkyl)-1,1,2-trimethyl-1H-benz(e)indo linium halide, preferably bromide, with sulfonatobutyl-1,1,2-trimethyl-1H-benz(e)indole at a relative molar ratio of about 0.9:1 to about 1:0.9, preferably 1:1 in an organic solvent, such as pyridine, and heated to reflux, followed by the addition of 1,3,3-trimethoxypropene in a relative molar ratio of about 1:1 to about 3:1 to the reaction product and continued reflux. The mixture subsequently is cooled and poured into an organic solvent such as ether. The resulting solid or semi-solid can be purified by chromatography on a silica gel column using a series of methanol/chloroform solvents.

As an alternative, two-step, synthesis procedure, also detailed in U.S. '709, N-4-sulfonatobutyl-1,1,2-trimethyl-1H-benz(e)indole and malonaldehyde bis(phenyl)mine)-monohydrochloride in a 1:1 molar ratio can be dissolved in acetic anhydride and the mixture heated. The acetic anhydride is removed under high vacuum and the residue washed with an organic solvent such as ether. The residual solid obtained is dried and subsequently mixed with the appropriate N-(carboxyalkyl)- or N-(hydroxyalkyl)-1,1,2-trimethyl-1H-benz(e)indo linium halide in the presence of an organic solvent, such as pyridine. The reaction mixture is heated, then the solvent is removed under vacuum, leaving the crude desired dye compound. The procedure was adapted from the two step procedure set forth in Ernst, L. A., et al., Cytometry 10:3-10 (1989).

The dyes also can be prepared with an amine or isothiocyanate terminating group. For example, N-(omega.-aminoalkyl)-1,1,2-trimethyl-1H-benz(e)indolenium bromide hydrobromide (synthesized as in N. Narayanan and G. Patonay, J. Org. Chem. 60:2391-5 (1995)) can be reacted to form dyes of formula 1 wherein R is —$NH_2$. Salts of these amino dyes can be converted to the corresponding isothiocyanates by treatment at room temperature with thiophosgene in an organic solvent such as chloroform and aqueous sodium carbonate.

These dyes have a maximum light absorption which occurs near 680 nm. They thus can be excited efficiently by commercially available laser diodes that are compact, reliable and inexpensive and emit light at this wavelength. Suitable commercially available lasers include, for example, Toshiba TOLD9225, TOLD9140 and TOLD9150, Phillips CQL806D, Blue Sky Research PS 015-00 and NEC NDL 3230SU. This near infrared/far red wavelength also is advantageous in that the background fluorescence in this region normally is low in biological systems and high sensitivity can be achieved.

The hydroxyl, carboxyl and isothiocyanate groups of the dyes provide linking groups for attachment to a wide variety of biologically important molecules, including proteins, peptides, enzyme substrates, hormones, antibodies, antigens, haptens, avidin, streptavidin, carbohydrates, oligosaccharides, polysaccharides, nucleic acids, deoxy nucleic acids, fragments of DNA or RNA, cells and synthetic combinations of biological fragments such as peptide nucleic acids (PNAs).

In another embodiment of the present invention, the ligands of the present invention may be conjugated to a lissamine dye, such as lissamine rhodamine B sulfonyl chloride. For example, a conjugable form of SR144528 may be conjugated with lissamine rhodamine B sulfonyl chloride to form a compound of the present invention.

Lissamine dyes are typically inexpensive dyes with attractive spectral properties. For example, examples have a molar extinction coefficient of 88,000 $cm^{-1}M^{-1}$ and good quantum efficient of about 95%. It absorbs at about 568 nm and emits at about 583 nm (in methanol) with a decent stokes shift and thus bright fluorescence.

The following are examples of dyes in conjugable form

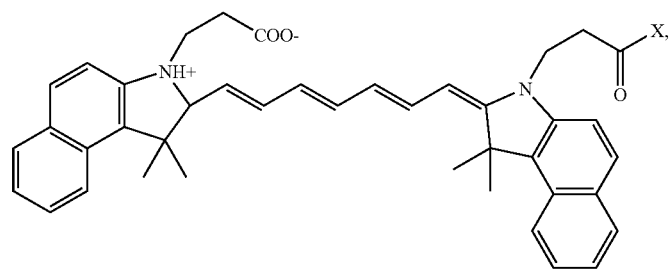

Cypate: X = Conjugation Site

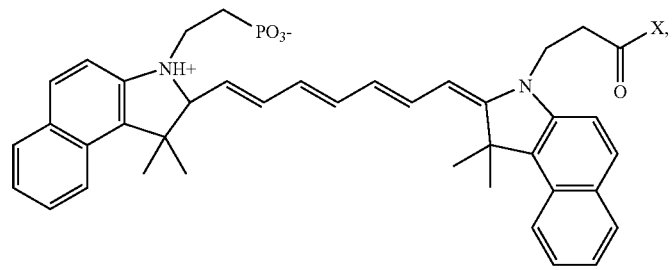

CY5.5: X = Conjugation Site

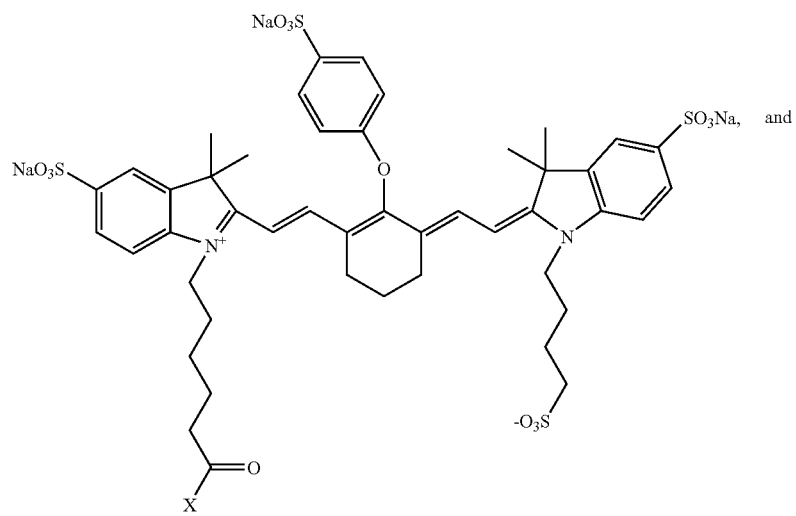
LI-COR 800CW: X Conjugation Site
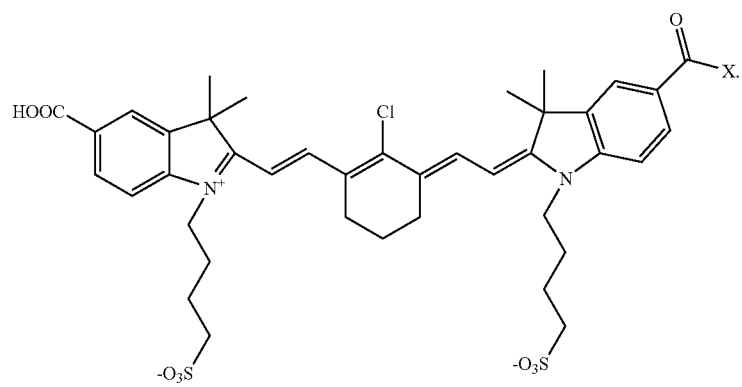
NIR-820: X Conjugation Site
Thus, a compound of the present invention is the following:
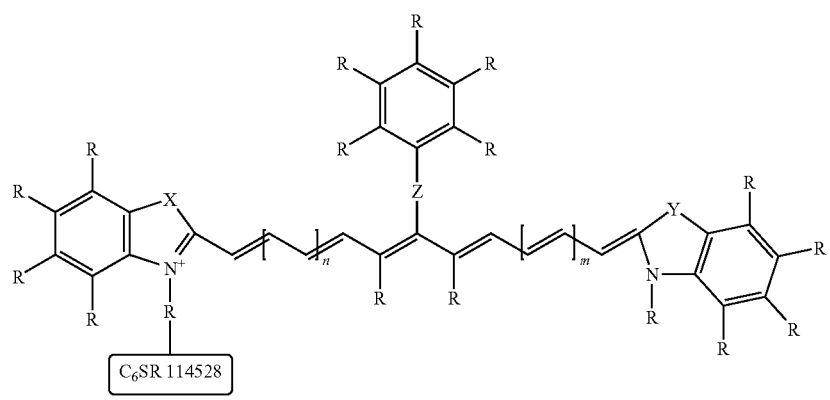

wherein the variables are defined in US patent application publication number 20060063247, incorporated herein by reference.

Additional examples of dyes usable with the present invention include dyes disclosed in U.S. Pat. No. 6,027,709. U.S. '709 discloses dyes which have the following general formula:

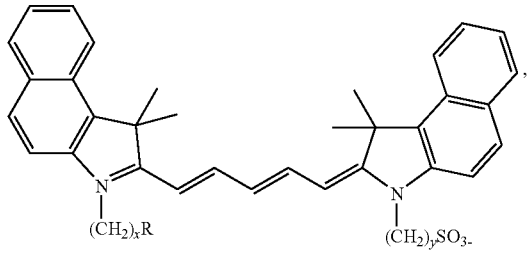

wherein R is —OH, —CO₂H, —NH₂, or —NCS and each of x and y, independently, is an integer selected from 1 to about 10. In preferred embodiments, each of x and y, independently, is an integer between about 2 and 6.

In one embodiment, the dye is N-(6-hydroxyhexyl)N'-(4-sulfonatobutyl)-3,3,3',3'-tetramethylbenz(e)indod icarbocyanine, which has the formula:

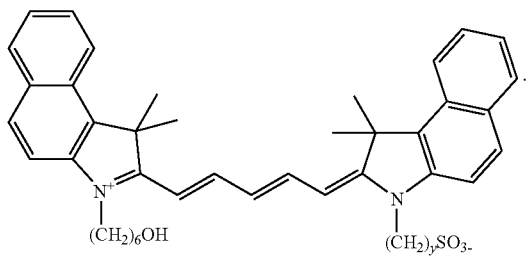

In a second embodiment, the dye is N-(5-carboxypentyl) N'-(4-sulfonatobutyl)3,3,3',3'-tetramethylbenz(e)indodicarbocyanine, which has the formula:

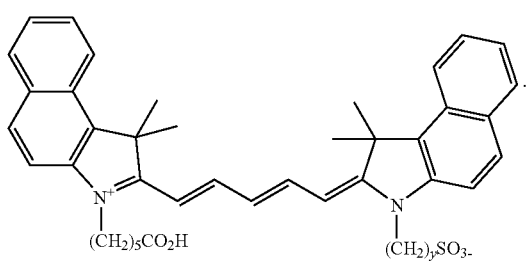

One embodiment of the present invention is the compound NIR-C₆SR144528.

As stated above, lanthanide chelates may be the signaling agents of the present invention.

Accordingly, embodiments of the present invention include the following compounds:

Thus, other embodiments of the present invention include the following compounds:

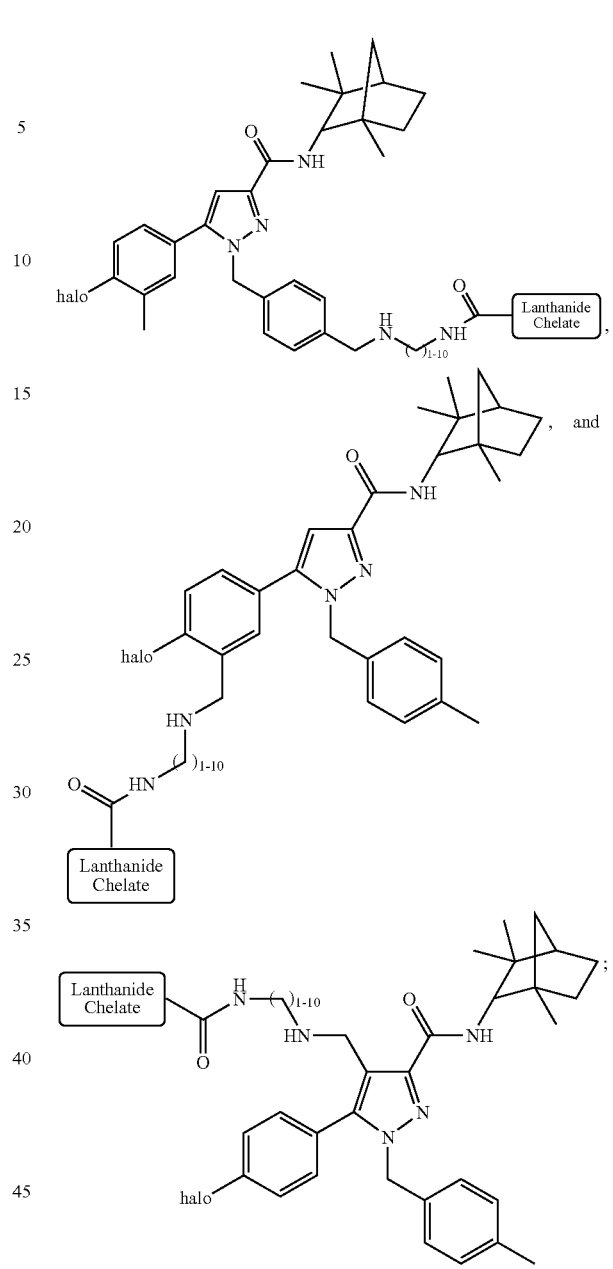

and analogs and conjugable forms thereof

In these embodiments, the lanthanide chelate compound may be of the following formula:

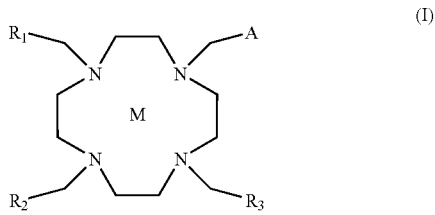

wherein:
M is a chelating ion selected from the group consisting of gallium (Ga), copper (Cu), nickel (Ni), indium (In), technetium (Tc), yttrium (Y) and lanthanide (Ln) series ions;

$R_1$ and $R_3$ are, independently,
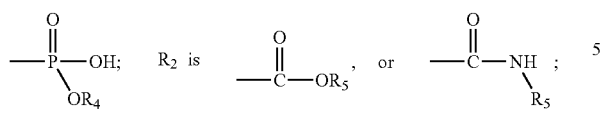
$R_4$ is H, $CH_3$, $C_2H_5$, $C_3H_7$, $C_4H_9$, $C_5H_{11}$, $C_6H_{13}$;
A is a sensitizer; and
$R_5$ is the conjugation site of the $CB_2$ receptor ligand of the present invention.
Examples of synthesizers include the following:
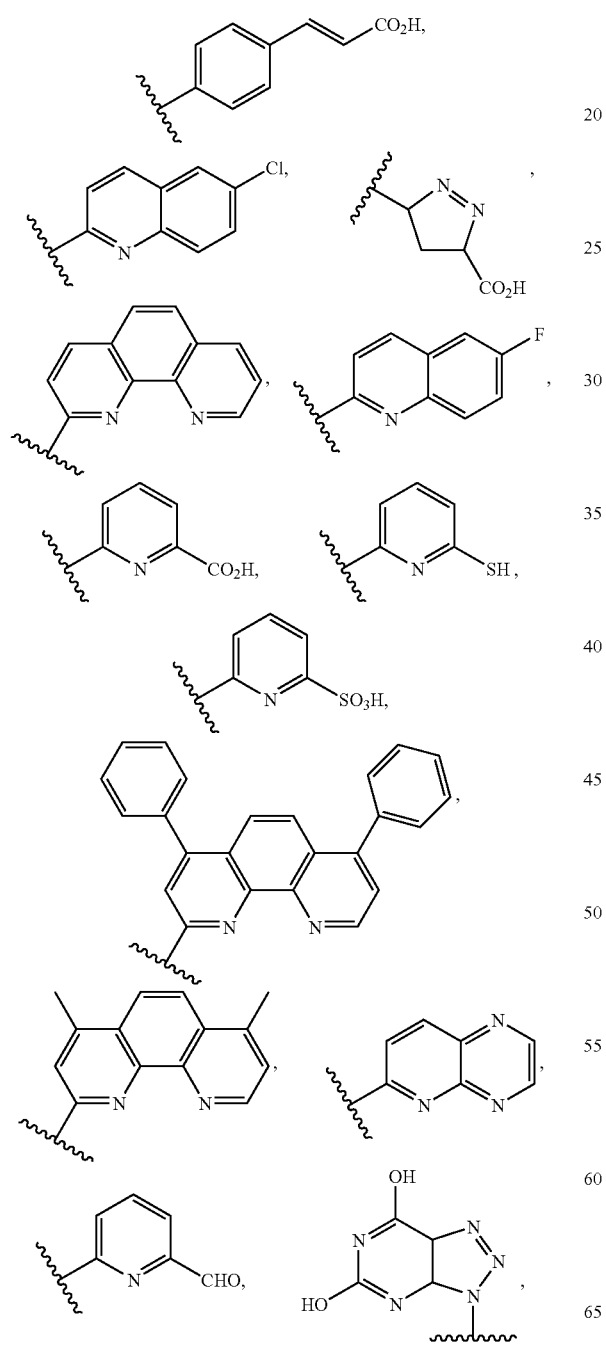
-continued
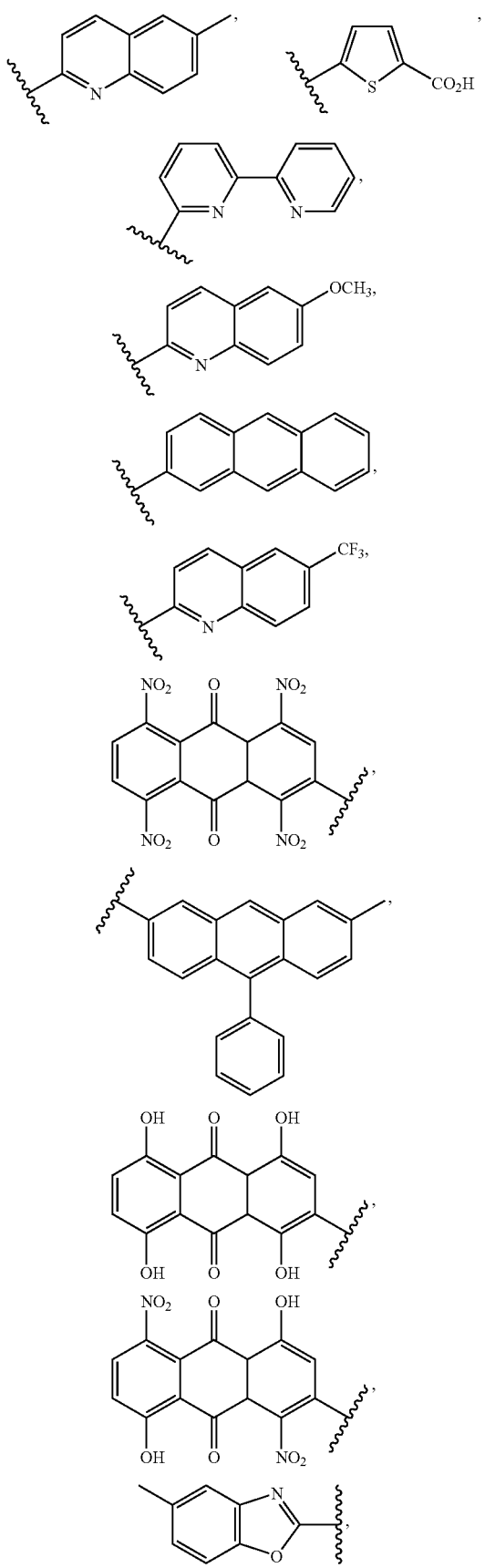

37
-continued
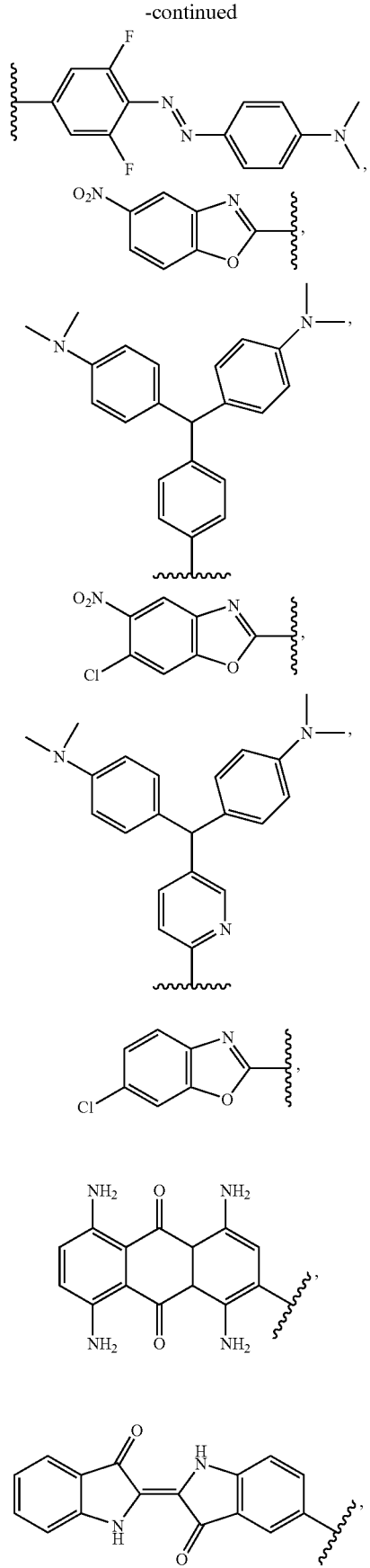
38
-continued
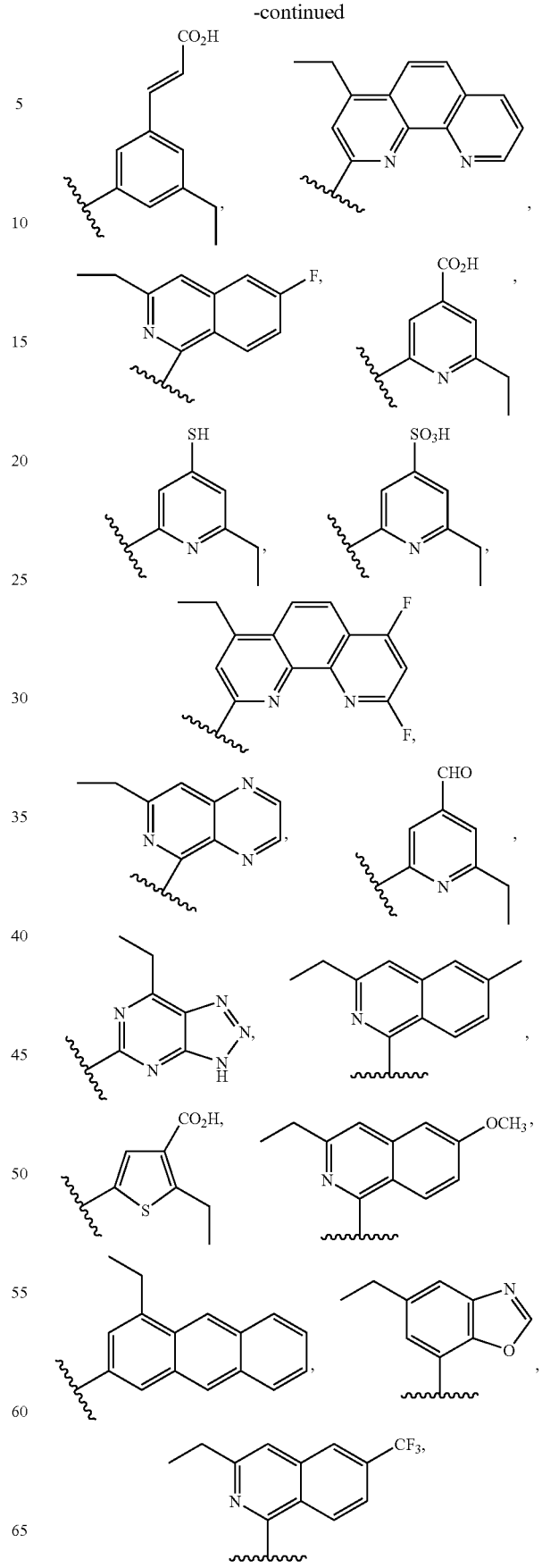

-continued
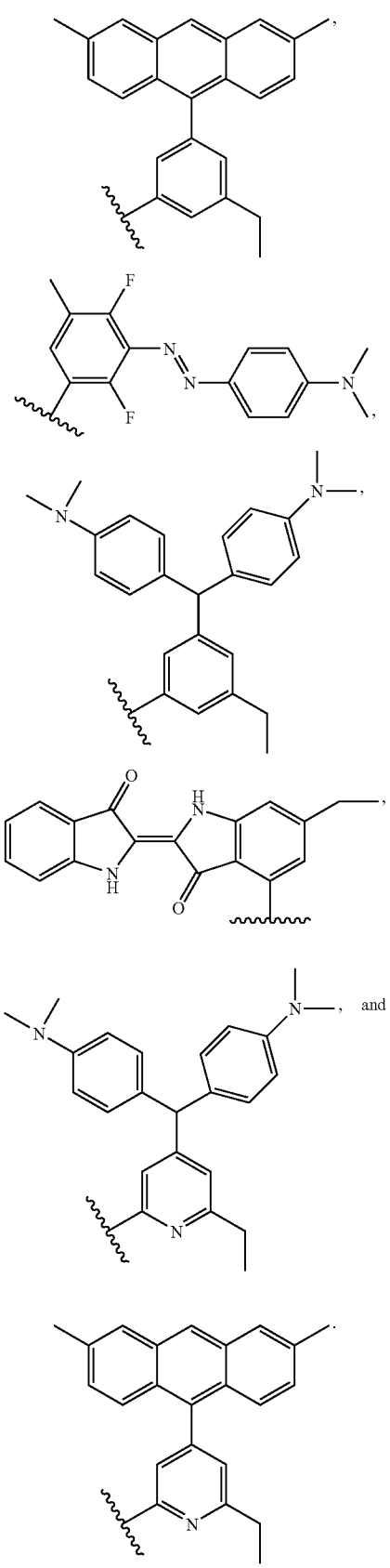
Preferably, A is
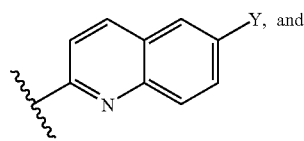
Y is F, Cl, CH₃, OCH₃, CF₃, or NO₂.
Additionally, M is a lanthanide series ion chosen from gadolinium (Gd), terbium (Tb), europium (Eu), ytterbium (Yb), neodymium (Nd), lutetium (Lu), erbium (Er) ions.
Other embodiments of the present invention include the following compounds:
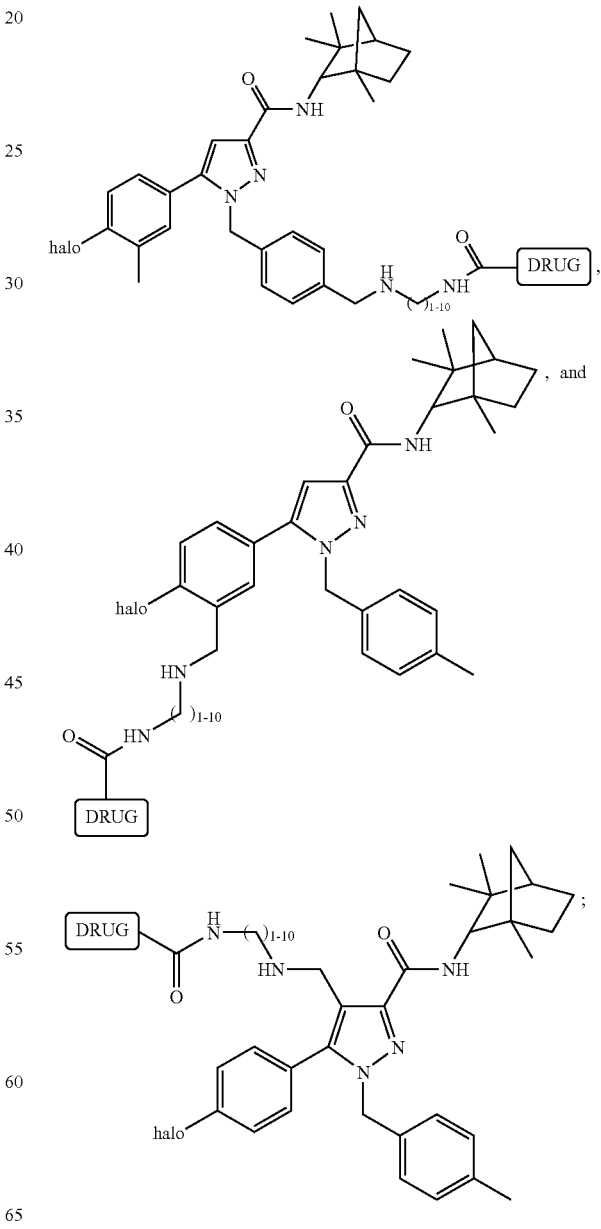
and analogs and conjugable forms thereof Additional embodiments include the following compounds:

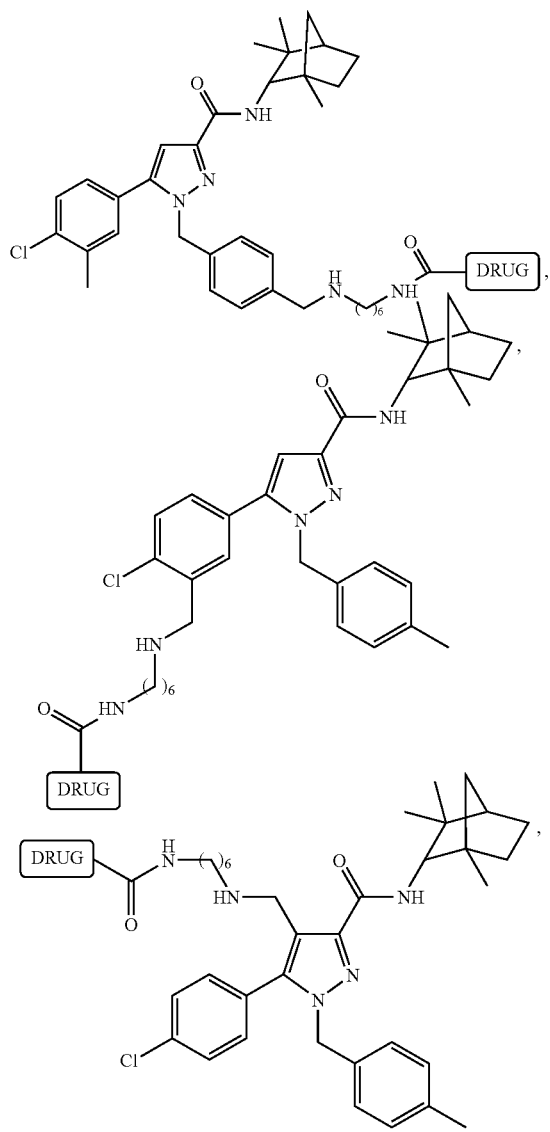

and stereoisomers thereof.

In embodiments of the invention DRUG is a topoisomerase inhibitor or a conjugable analog thereof. The topoisomerase inhibitor is selected from the group consisting of adriamycin, amsacrine, camptothecin, daunorubicin, dactinomycin, doxorubicin, eniposide, epirubicin, etoposide, idarubicin, mitoxantrone, teniposide, and topotecan.

In other embodiments of the invention, DRUG is etopiside or a conjugable analog thereof. Etoposide is one of the most widely used anticancer drugs and is active against small-cell lung cancers, leukemias, and lymphomas.

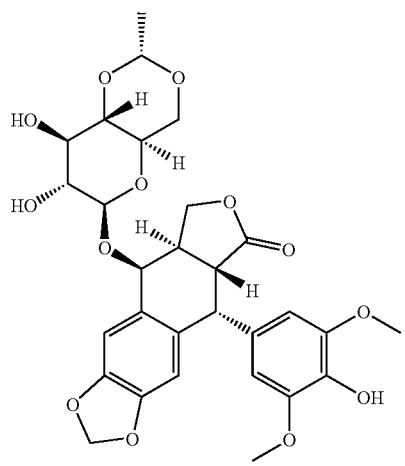

Etoposide compound

Thus, embodiments of the invention include the following compounds:

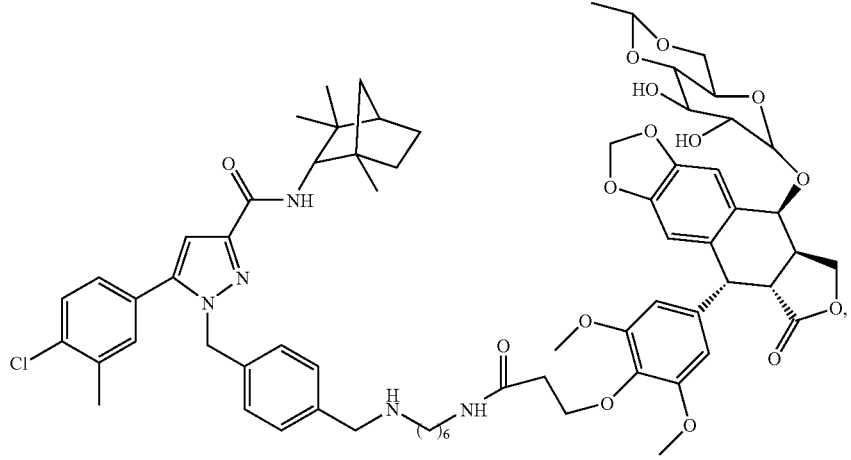

-continued

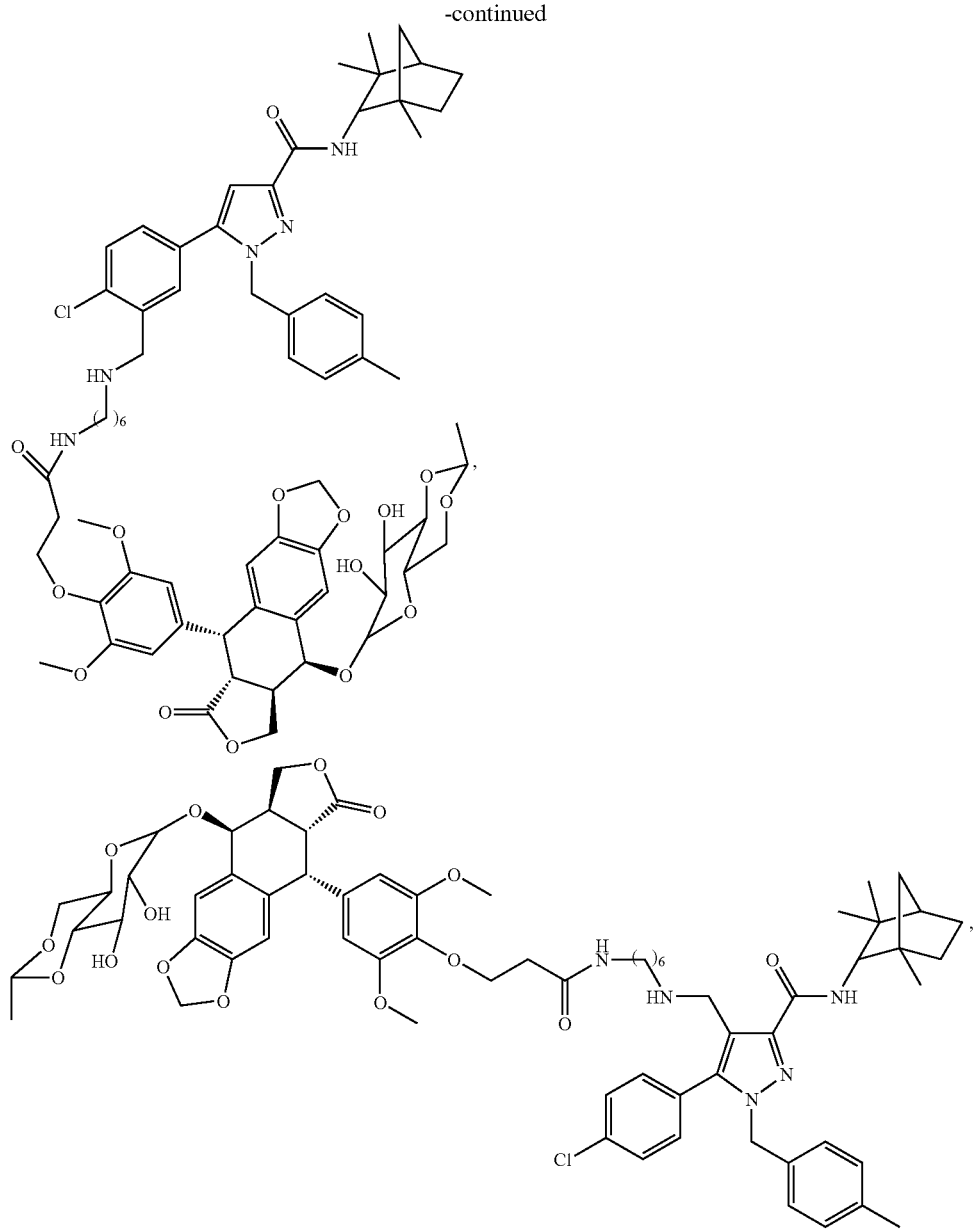

and stereoisomers thereof.

The imaging and/or therapeutic agents of the present invention may be administered as determined by one of ordinary skill in the art. In embodiments the agents may be administered as shown in U.S. application Ser. No. 11/181,201, incorporated herein by reference.

That is, compounds of the present invention can be administered orally, parenterally by intravenous injection, transdermally, by pulmonary inhalation, by intravaginal or intrarectal insertion, by subcutaneous implantation, intramuscular injection or by injection directly into an affected tissue, as for example by injection into a tumor site. In some instances the materials may be applied topically at the time surgery is carried out. In another instance the topical administration may be ophthalmic, with direct application of the therapeutic composition to the eye.

The materials are formulated to suit the desired route of administration. The formulation may comprise suitable excipients include pharmaceutically acceptable buffers, stabilizers, local anesthetics, and the like that are well known in the art. For parenteral administration, an exemplary formulation may be a sterile solution or suspension; For oral dosage, a syrup, tablet or palatable solution; for topical application, a lotion, cream, spray or ointment; for administration by inhalation, a microcrystalline powder or a solution suitable for nebulization; for intravaginal or intrarectal administration, pessaries, suppositories, creams or foams. Preferably, the route of administration is parenteral, more preferably intravenous.

In general, an embodiment of the invention is to administer a suitable daily dose of a therapeutic composition that will be the lowest effective dose to produce a therapeutic effect. However, it is understood by one skilled in the art that the dose of the composition to practice the invention will vary depending on the subject and upon the particular route of administration used. It is routine in the art to adjust the dosage to suit the individual subjects. Additionally, the effective amount may be based upon, among other things, the size of the compound, the biodegradability of the compound, the bioactivity of the compound and the bioavailability of the compound. If the compound does not degrade quickly, is bioavailable and highly active, a smaller amount will be required to be effective. The actual dosage suitable for a subject can easily be determined as a routine practice by one skilled in the art, for example a physician or a veterinarian given a general starting point.

The therapeutic treatment may be administered hourly, daily, weekly, monthly, yearly (e.g., in a time release form) or as a one-time delivery. The delivery may be continuous delivery for a period of time, e.g., intravenous delivery. In one embodiment of the methods described herein, the therapeutic composition is administered at least once per day. In one embodiment, the therapeutic composition is administered daily. In one embodiment, the therapeutic composition is administered every other day. In one embodiment, the therapeutic composition is administered every 6 to 8 days. In one embodiment, the therapeutic composition is administered weekly.

In embodiments of the methods described herein, the route of administration can be oral, intraperitoneal, transdermal, subcutaneous, by vascular injection into the tumor, by intravenous or intramuscular injection, by inhalation, topical, intralesional, infusion; liposome-mediated delivery; intrathecal, gingival pocket, rectal, intrabronchial, nasal, transmucosal, intestinal, ocular or otic delivery, or any other methods known in the art as one skilled in the art may easily perceive. In other embodiments of the invention, the compositions incorporate particulate forms protective coatings, hydrolase inhibitors or permeation enhancers for various routes of administration, including parenteral, pulmonary, nasal and oral.

An embodiment of the method of present invention is to administer the compositions described herein in a sustained release form. Such method comprises implanting a sustained-release capsule or a coated implantable medical device so that a therapeutically effective dose is continuously delivered to a subject of such a method. The compositions may be delivered via a capsule which allows sustained-release of the agent or the peptide over a period of time. Controlled or sustained-release compositions include formulation in lipophilic depots (e.g., fatty acids, waxes, oils). Also comprehended by the invention are particulate compositions coated with polymers (e.g., poloxamers or poloxamines).

The method of present invention is effective in treatment of various types of cancers, including but not limited to: glioblastomas, pancreatic cancer, renal cell cancer, Kaposi's sarcoma, chronic leukemia (preferably chronic myelogenous leukemia), chronic lymphocytic leukemia, breast cancer, sarcoma, ovarian carcinoma, rectal cancer, throat cancer, melanoma, colon cancer, bladder cancer, lymphoma, mesothelioma, mastocytoma, lung cancer, liver cancer, mammary adenocarcinoma, pharyngeal squamous cell carcinoma, gastrointestinal cancer, stomach cancer, myeloma, prostate cancer, B-cell malignancies or metastatic cancers.

The present invention is also effective against other diseases related to unwanted cell proliferation. Such hyperproliferative diseases include but are not limited to: psoriasis, rheumatoid arthritis, lamellar ichthyosis, epidermolytic hyperkeratosis, restenosis, endometriosis, proliferative retinopathy, lung fibrosis, desmoids or abnormal wound healing.

Additionally, based on the present invention's affinity for the $CB_2$ receptor, the present invention is also useful in treating pain, inflammation, osteoporosis, immunological disorders, etc.

EXAMPLES

Example 1

This Example demonstrates synthesis of DOTA derivatives. The synthesis of DOTA derivatives 28-30 was achieved into two steps (scheme 4): the coupling reaction between conjugable compounds (6, 14 and 24) and the DOTA-mono-NHS-tris(tert-butyl) ester (25-27), followed by the hydrolysis of the tert-butyl ester functions using trifluoroacetic acid. Chelation of gadolinium was next performed using gadolinium(III) trifluoromethane sulfonate under basic conditions (31-33).

Scheme 4. Synthesis of compounds 31-33[a]

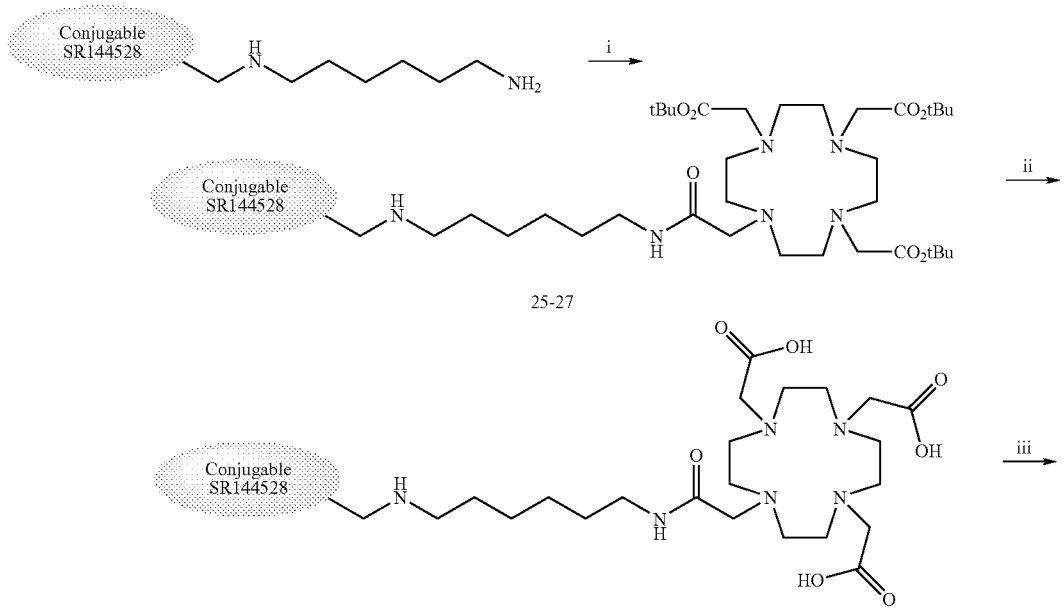

25-27

28-30

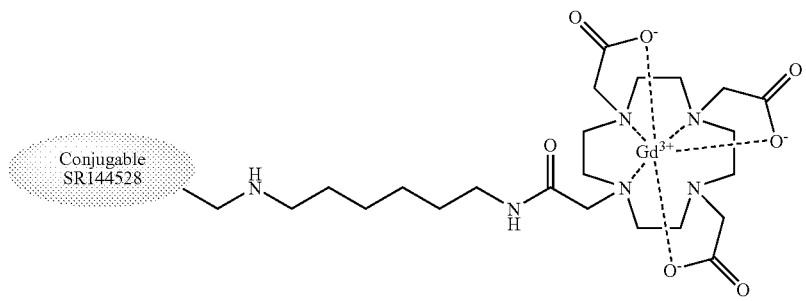

31-33

[a]Reagents and conditions: (i) 1,4,7,10-tetraazacyclododecane-1,4,7-tris(t-butyl acetate)-10-succinimidyl acetate, TEA, dry CH$_2$Cl$_2$, atm N$_2$, rt, 65-70%; (ii) trifluoroacetic acid, atm N$_2$, rt, 82-88%; (iii) gadolinium(III)trifluoromethane sulfonate, NaOH, MeOH, atm N$_2$, rt, 40-45%.

Example 2

This example demonstrates synthesis of ES55 and ES58.

Near-Infrared (NIR) derivatives ES55 and ES58 were obtained by conjugation of 14 and 24 with IRDye® 800CW NHS ester. The reaction was monitored by analytical HPLC at 780 nm. NIR-compounds were purified using a semi-preparative HPLC.

Scheme 5. Synthesis of compounds ES55 and ES58[a]

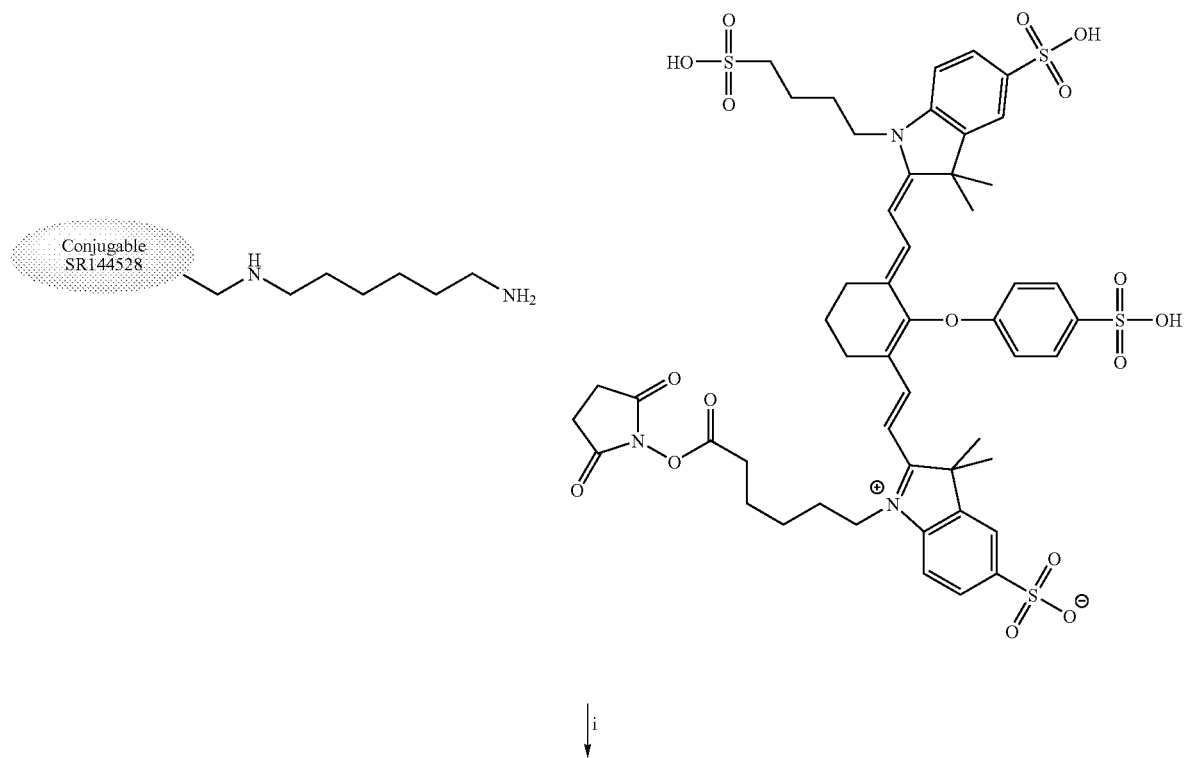

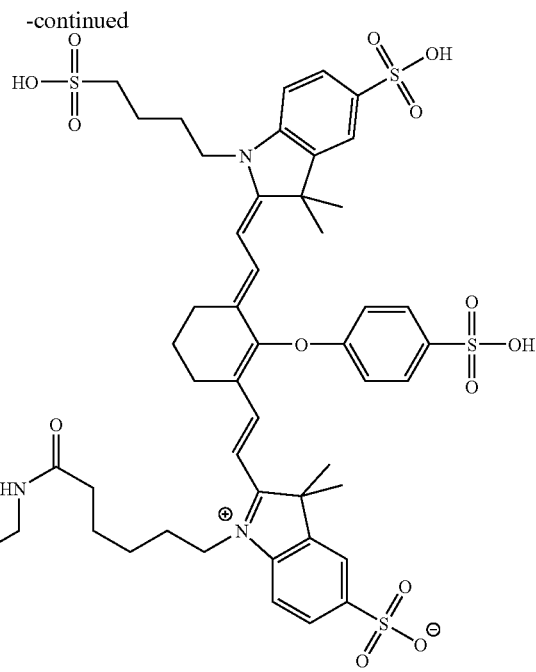

-continued

[a]Reagents and conditions: (i) DMSO, atm $N_2$, rt, 93-94%

Example 3

This Example demonstrates spectroscopic characterization of embodiments of the present invention.

Figure 4:
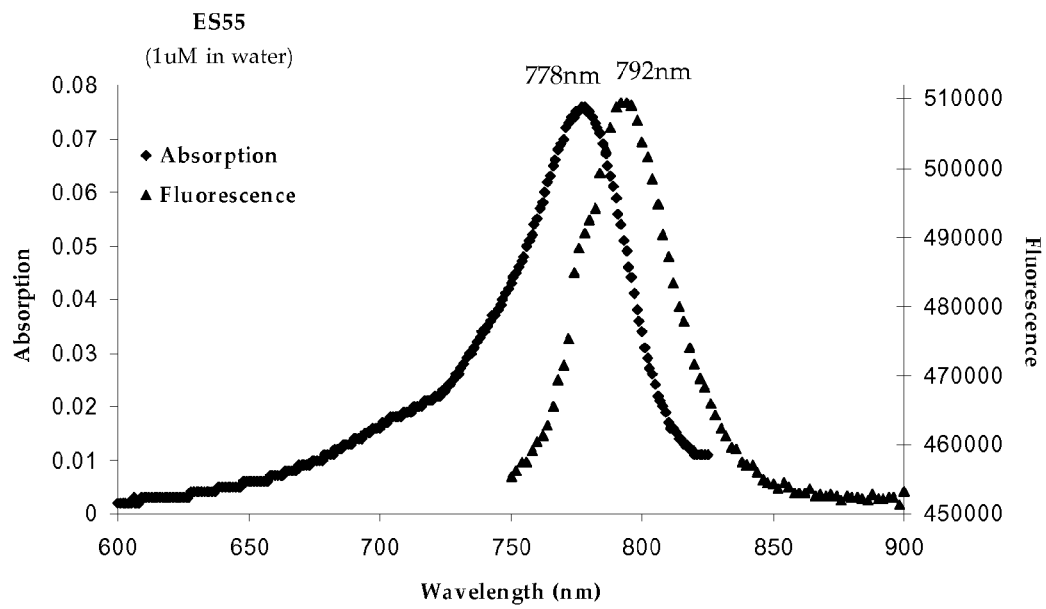
FIGS. 4 and 5 show absorbance spectra of embodiments of the present invention.
Figure 5:
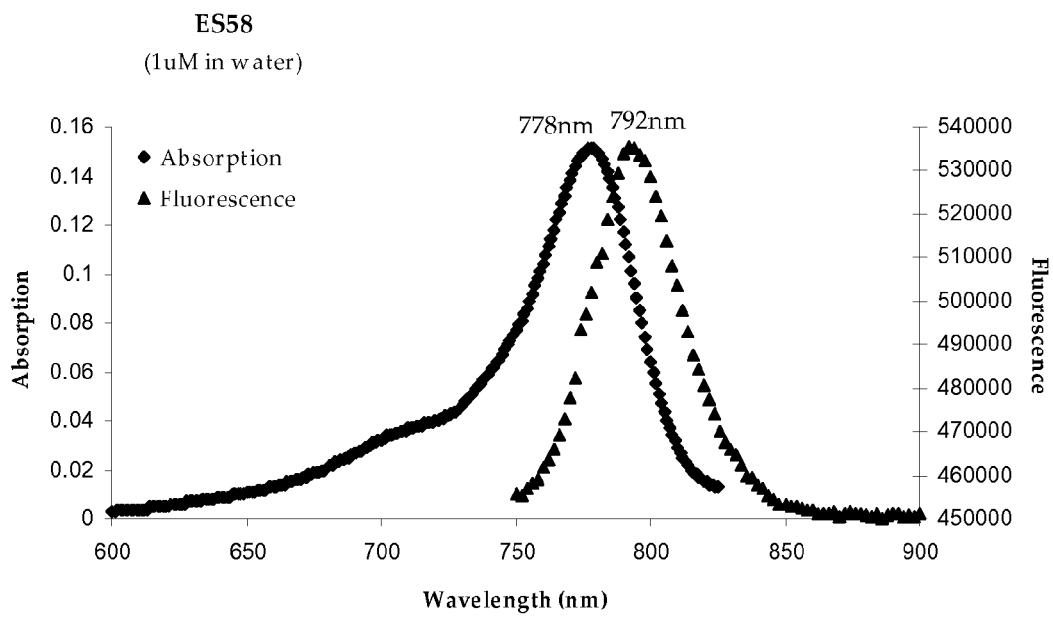

The absorbance spectra of ES55 and ES58 were measured using a Shimadzu UV-VIS 1700 spectrophotometer (Columbia, Md.) and the emission spectra were measured using a PTI Technologies spectrofluorometer (Oxnard, Calif.; excitation wavelength: 778 nm, 1 nm/second scan rate, 1.5 nm slit width and 75 watts Photomultiplier tube voltage). See FIGS. 4 and 5

Example 4

Figure 6:
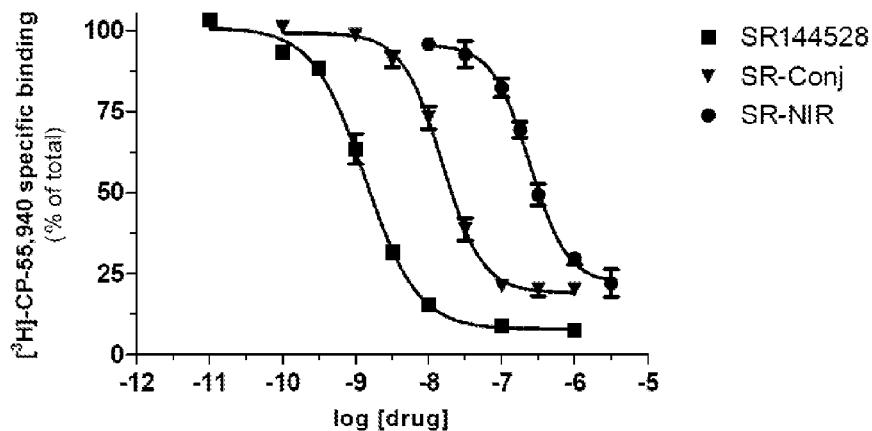
FIGS. 6 and 7 are graphs that show absorption and fluorescence of embodiments of the present invention.

One NIR dye labeled conjugable SR144528 (NIRmbc94 or SR-NIR) was tested for its ability to displace the binding of [$^3$H]-SR144528 to membrane fractions from DBT cells stably expressing mouse CB2 receptors. See FIG. 6.

The present inventors found that SR144528 had a Ki of 0.7 nM, which is in agreement with published reports, and that SR-Conj ($C_6$SR144528: i.e. mbc94) had a Ki of 15 nM and SR-NIR (NIRmbc94) had a Ki of 120 nM.

Figure 7:
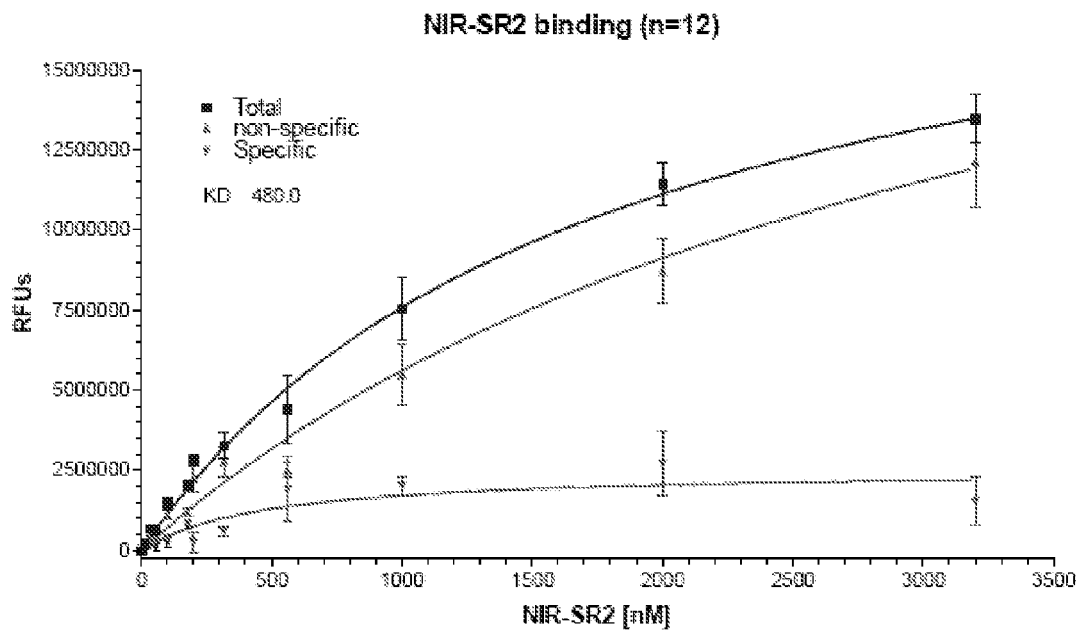

The compound was then tested for its ability to specifically label intact CB2-expressing DBT cells in culture. Total binding was determined in CB2-expressing DBT cells and non-specific binding was determined in wild-type DBT cells, which are devoid of CB2 receptors (as ascertained by quantitative PCR). See FIG. 7.

The present inventors found that NIR-SR2 (NIRmbc94) binds specifically to CB2-expressing DBT cells with a Kd of 480 mM.

REFERENCES

Throughout this application, various publications are cited. The publications, including those listed below, are incorporated herein by reference in their entirety.

Munro, S.; Thomas, K. L.; Abushaar, M. (1993) Molecular Characterization of a Peripheral Receptor for Cannabinoids. *Nature* 365, 61-65.

Matsuda, L. A.; Lolait, S. J.; Brownstein, M. J.; Young, A. C.; Bonner, T. I. (1990) Structure of a Cannabinoid Receptor and Functional Expression of the Cloned Cdna. *Nature* 346, 561-564.

Pertwee, R. G. (1997) Pharmacology of cannabinoid CB1 and CB2 receptors. *Pharmacology & Therapeutics* 74, 129-180.

Galiegue, S.; Mary, S.; Marchand, J.; Dussossoy, D.; Carriere, D. et al. (1995) Expression of Central and Peripheral Cannabinoid Receptors in Human Immune Tissues and Leukocyte Subpopulations. *European Journal of Biochemistry* 232, 54-61.

Femandez-Ruiz, J.; Romero, J.; Velasco, G.; Tolon, R. M.; Ramos, J. A. et al. (2007) Cannabinoid CB2 receptor: a new target for controlling neural cell survival? *Trends in Pharmacological Sciences* 28, 39-45.

Malan, T. P.; Ibrahim, M. M.; Lai, J.; Vanderah, T. W.; Makriyannis, A. et al. (2003) CB2 cannabinoid receptor agonists: pain relief without psychoactive effects? *Current Opinion in Pharmacology* 3, 62-67.

Malan, T. P.; Ibrahim, M. M.; Deng, H. F.; Liu, Q.; Mata, H. P. et al. (2001) CB2 cannabinoid receptor-mediated peripheral antinociception. *Pain* 93, 239-245.

Iwamura, H.; Suzuki, H.; Ueda, Y.; Kaya, T.; Inaba, T. (2001) In vitro and in vivo pharmacological characterization of JTE907, a novel selective ligand for cannabinoid CB2 receptor. *Journal of Pharmacology and Experimental Therapeutics* 296, 420-425.

Karsak, M.; Ofek, O.; Fogel, M.; Wright, K.; Tam, J. et al. (2004) The cannabinoid CB2 receptor: A potential target for the diagnosis and treatment of osteoporosis. *Journal of Bone and Mineral Research* 19, S383-S383.

Sanchez, C.; de Ceballos, M. L.; del Pulgar, T. G.; Rueda, D.; Corbacho, C. et al. (2001) Inhibition of glioma growth in vivo by selective activation of the CB2 cannabinoid receptor. *Cancer Research* 61, 5784-5789.

McKallip, R. J.; Lombard, C.; Fisher, M.; Martin, B. R.; Ryu, S. H. et al. (2002) Targeting CB2 cannabinoid receptors as a novel therapy to treat malignant lymphoblastic disease. *Blood* 100, 627-634.

Walter, L.; Stella, N. (2004) Cannabinoids and neuroinflammation. *British Journal of Pharmacology* 141, 775-785.

Pertwee, R. G. (2002) Cannabinoids and multiple sclerosis. *Pharmacology & Therapeutics* 95, 165-174.

Gaoni, Y.; (1964) Mechoulam, R. Isolation, Structure, and Partial Synthesis of an Active Constituent of Hashish. *Journal of the American Chemical Society* 86, 1646-1647.

Witting, A.; Stella, N. (2004) Cannabinoid Signaling in Glial Cells in Health and Disease. *Current Neuropharmacology* 2, 115-124.

Mackie, K.; Stella, N. (2006) Cannabinoid receptors and endocannabinoids: Evidence for new players. *Aaps Journal* 8, E298-E306.

Piomelli, D. (2005) The endocannabinoid system: a drug discovery perspective. *Curr Opin Investig Drugs* 6, 672-679.

Pertwee, R. G.; Ross, R. A. (2002) Cannabinoid receptors and their ligands. *Prostaglandins Leukotrienes and Essential Fatty Acids* 66, 101-121.

Oka, S.; Ikeda, S.; Kishimoto, S.; Gokoh, M.; Yanagimoto, S. et al. (2004) 2-Arachidonoylglycerol, an endogenous cannabinoid receptor ligand, induces the migration of EoL-1 human eosinophilic leukemia cells and human peripheral blood eosinophils. *Journal of Leukocyte Biology* 76, 1002-1009.

Roy, A. K.; Batra, S. (2003) Facile Baylis-Hillman reaction of substituted 3-isoxazolecarbaldehydes: The impact of a proximal heteroatom within a heterocycle on the acceleration of the reaction. *Synthesis-Stuttgart* 2325-2330.

Seltzman, H. H.; Foster, M. C.; Wyrick, C. D.; Burgess, J. P.; Carroll, F. I. (2005) Tritiation of the cannabinoid receptor antagonist SR144528 involving lithium aluminum tritide reduction; assessment of the kinetic isotope effect by H-3-NMR. *Journal of Labelled Compounds & Radiopharmaceuticals* 48, 589-596.

Suchocki, J. A.; May, E. L.; Martin, T. J.; George, C.; Martin, B. R. (1991) Synthesis of 2-Exo-Mecamylamine and 2-Endo-Mecamylamine Analogs—Structure-Activity-Relationships for Nicotinic Antagonism in the Central-Nervous-System. *Journal of Medicinal Chemistry* 34, 1003-1010.

Weissleder, R. (2001) A clearer vision for in vivo imaging. *Nature Biotechnology* 19, 316-317.

Shah, K.; Weissleder, R. (2005) Molecular optical imaging: applications leading to the development of present day therapeutics. *The American Society for Experimental NeuroTherapeutics* 2, 215-225.

Raitio, K. H.; Salo, O. M. H.; Nevalainen, T.; Poso, A.; Jarvinen, T. Targeting the cannabinoid CB2 receptor: Mutations, modeling and development of CB2 selective ligands. *Current Medicinal Chemistry* 2005, 12, 1217-1237.

Rinaldi-Carmona, M.; Barth, F.; Millan, J.; Derocq, J. M.; Casellas, P. et al. SR 144528, the first potent and selective antagonist of the CB2 cannabinoid receptor. *Journal of Pharmacology and Experimental Therapeutics* 1998, 284, 644-650.

The invention thus being described, it will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification, including the Examples and Attachment be considered as exemplary only, and not intended to limit the scope and spirit of the invention.

Unless otherwise indicated, all numbers expressing quantities of ingredients, properties such as reaction conditions, and so forth used herein are to be understood as being modified in all instances by the term "about." Accordingly, unless indicated to the contrary, the numerical parameters set forth in the herein are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

We claim:

1. A compound of the following formula:

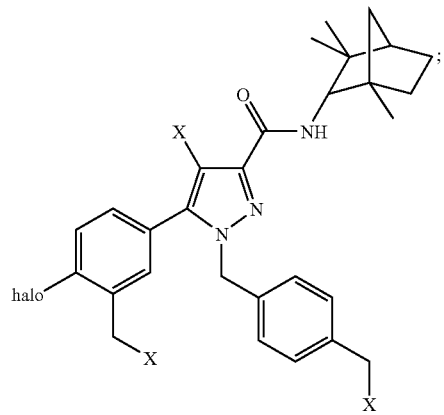

wherein X is H or substituted with

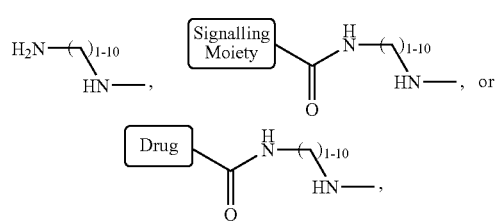

with at least one X being substituted; and halo is fluorine, chlorine, bromine, iodine;

and stereoisomers and conjugable analogs thereof.

2. The compound of claim 1, wherein signaling moiety is chosen from a lanthanide chealate or a dye.

3. The compound of claim 2, wherein the dye is a NIR dye.

4. The compound of claim 2, wherein the dye is:

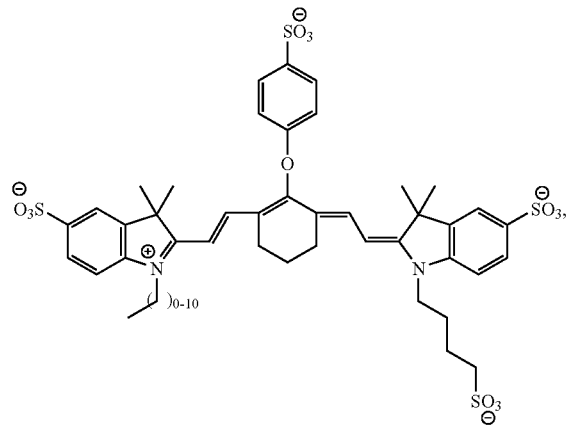

and stereoisomers thereof.

5. The compound of claim 2, wherein the lanthanide chelate is

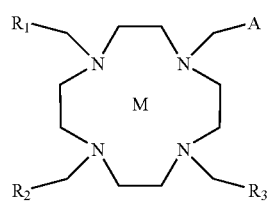

(I)

wherein:

M is a chelating ion selected from the group consisting of gallium (Ga), copper (Cu), nickel (Ni), indium (In), technetium (Tc), yttrium (Y) and lanthanide (Ln) series ions;

$R_1$ and $R_3$ are, independently, $R_2$ is

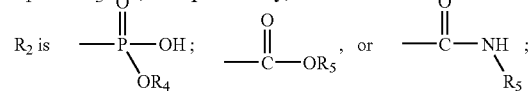

$R_4$ is H, $CH_3$, $C_2H_5$, $C_3H_7$, $C_4H_9$, $C_5H_{11}$, $C_6H_{13}$;

A is a sensitizer; and $R_5$ is the conjugation site of the $CB_2$ receptor ligand of the present invention.

6. A compound of claim 1, of the following formula:

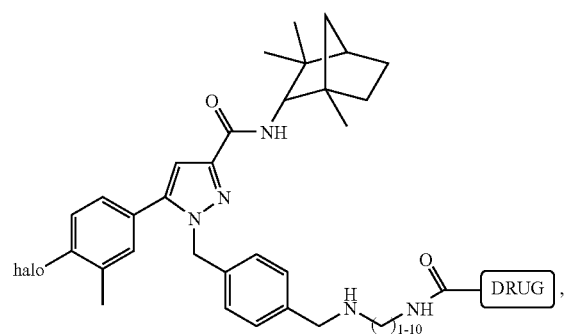

-continued

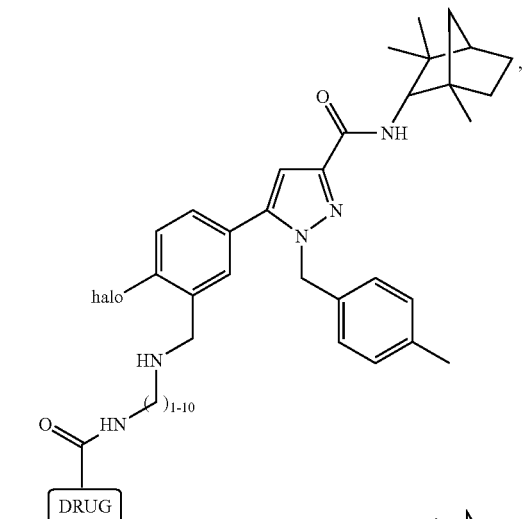

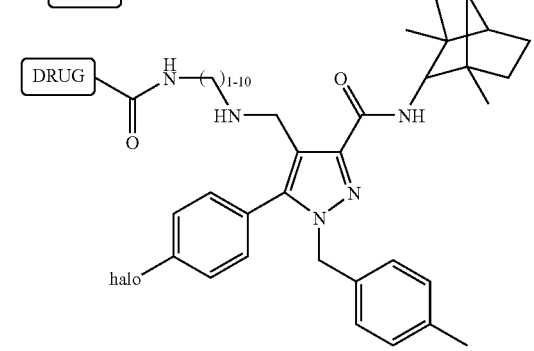

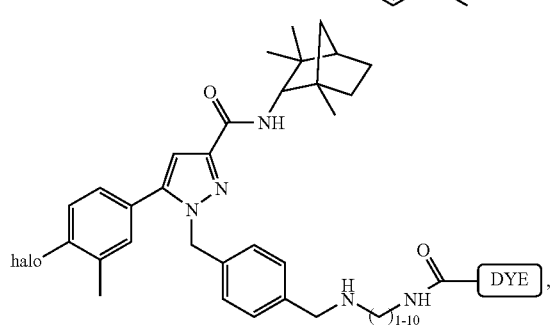

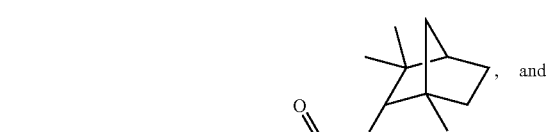

, and

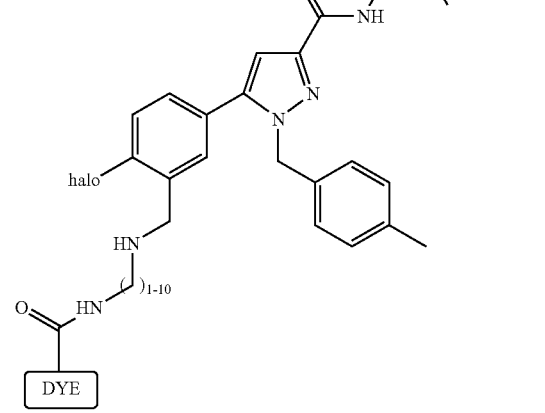

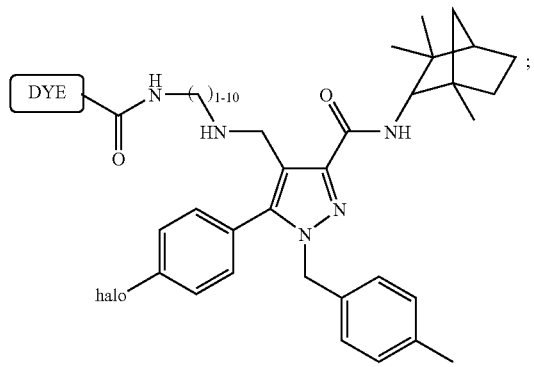
and stereoisomers and conjugable forms thereof.
7. The compound of claim 6, wherein halo is chlorine.
8. The compound of claim 1, of the following formula:
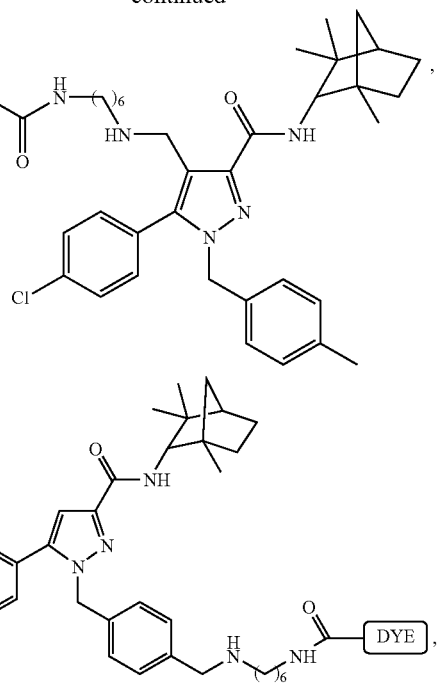
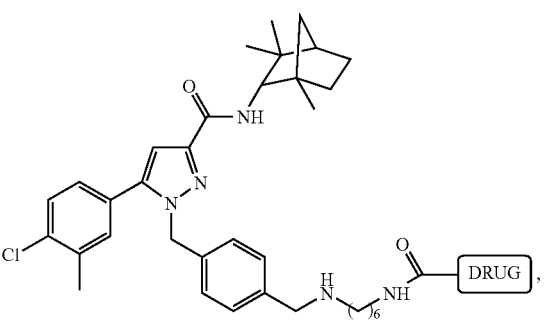
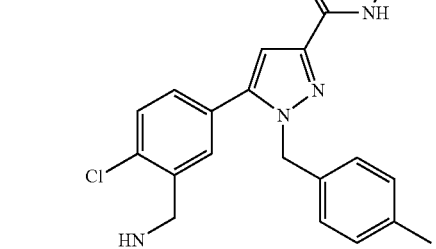
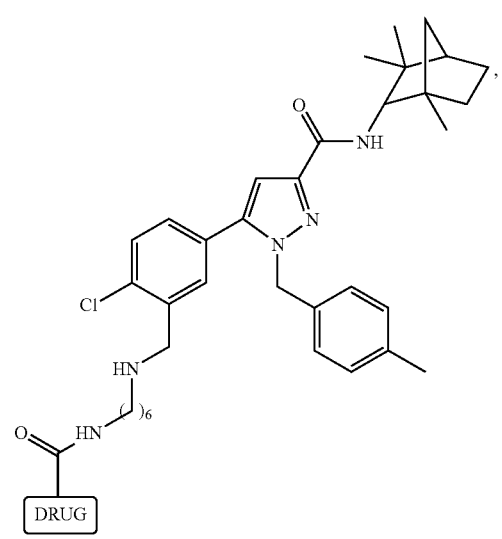
and stereoisomers and conjugable forms thereof.
9. The compound of claim 1, wherein DRUG is etopiside or a conjugable analog thereof.

10. A compound of claim 1, of the following formula:
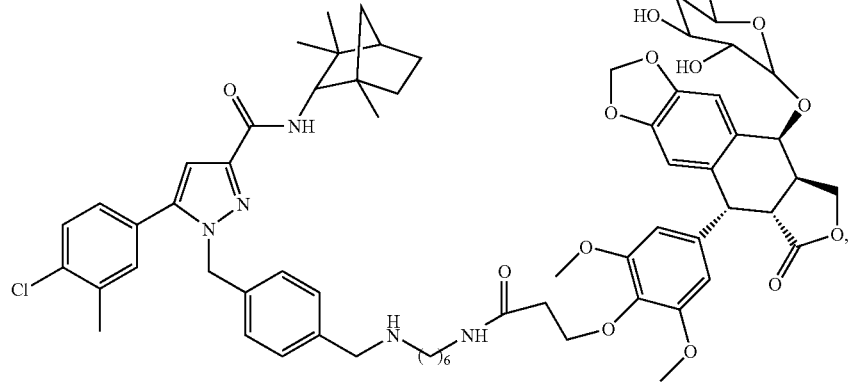
and stereoisomers thereof.
11. A compound of claim 1, of the following formula:
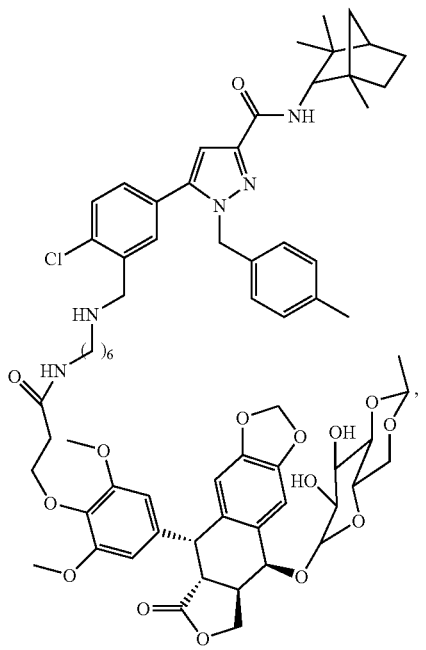
and stereoisomers thereof.

12. A compound of claim 1, of the following formula:
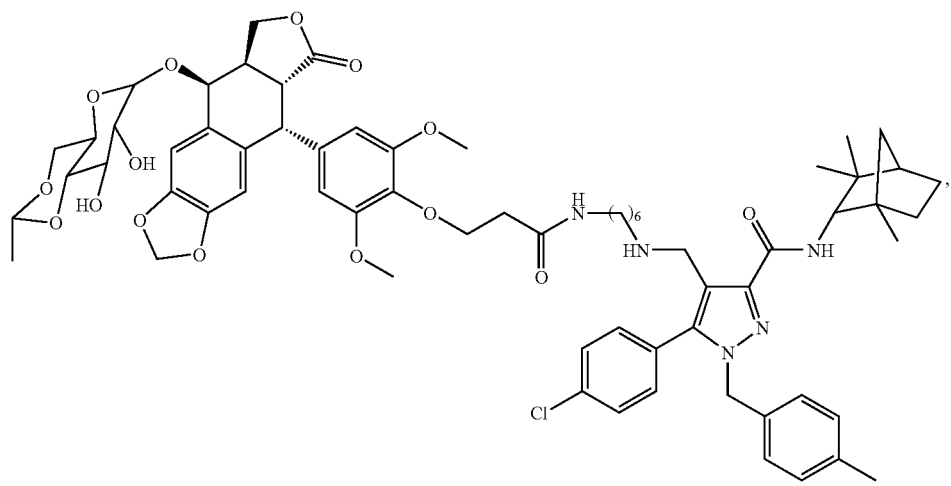
and stereoisomers thereof.
13. A conjugate comprising:
a compound of the following formula:
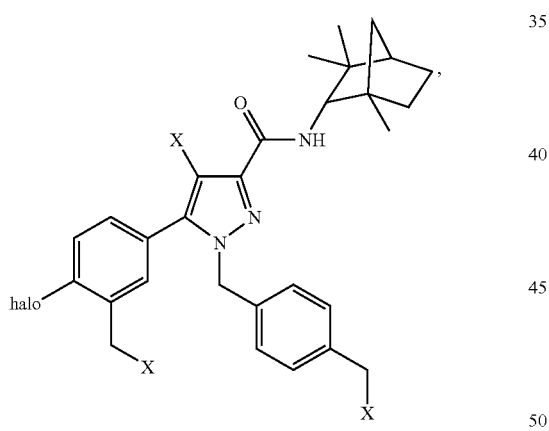
wherein X is H or substituted with
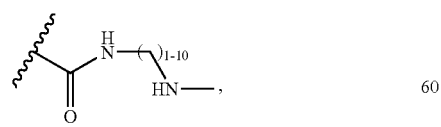
with at least X being substituted; and halo is fluorine, chlorine, bromine, iodine, and stereoisomers and conjugable analogs thereof; and
an imaging agent or therapeutic agent binded thereto.

14. The conjugate of claim 13, of the following formula:
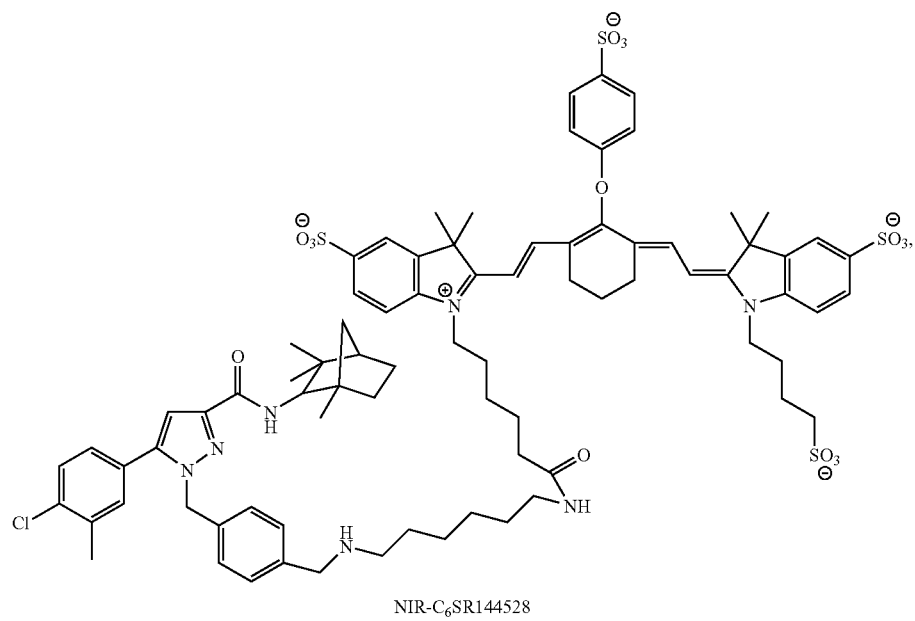
NIR-C$_6$SR144528
and stereoisomers thereof.
15. The conjugate of claim 13, of the following formula:
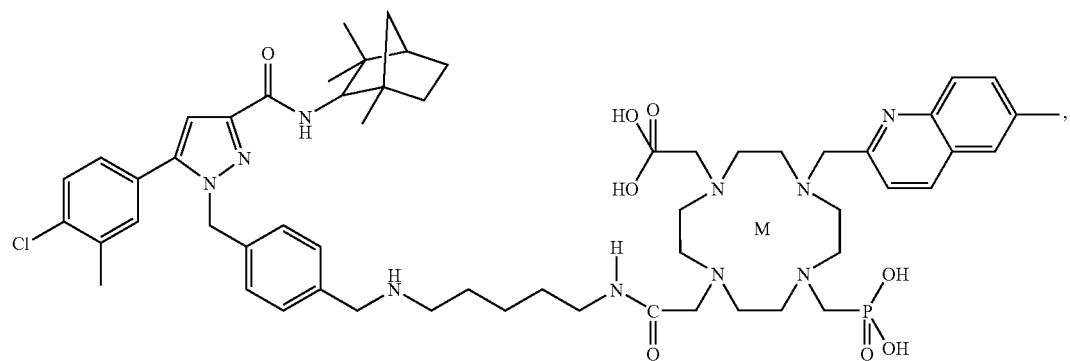
wherein M is chelating ion selected from the group consisting of gallium (Ga), copper (Cu), nickel (Ni), indium (In), technetium (Tc), yttrium (Y), lutetium (Lu) and lanthanide (Ln) series ions;
and stereoisomers thereof.

16. The conjugate of claim 13, of the following formula:

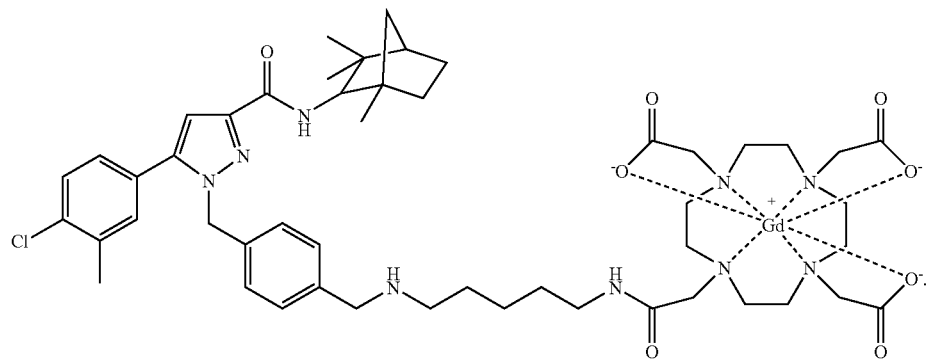

17. The conjugate of claim 13, of the following formula:

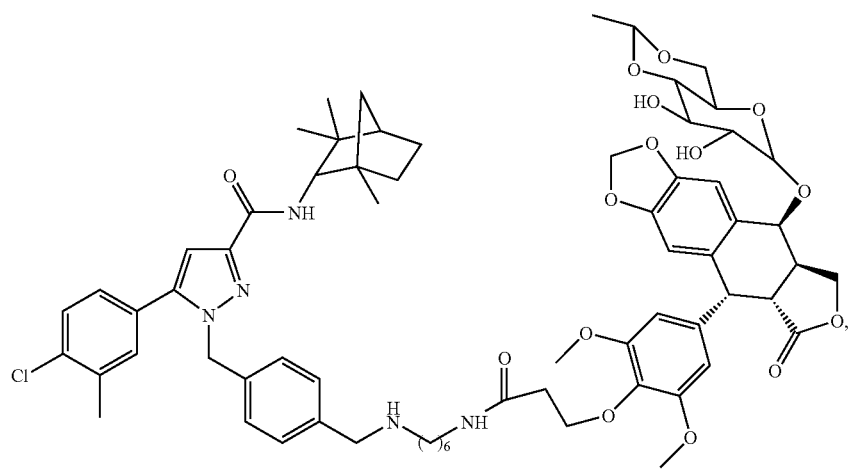

and stereoisomers thereof.

18. The conjugate of claim 13, wherein the imaging agent is an NIR dye, and conjugable analogs thereof.

19. The conjugate of claim 13, wherein the therapeutic agent is etopiside or a conjugable analog thereof.

20. A method for delivering an agent to a sample of cells, comprising:

(a) forming a conjugate of following formula:

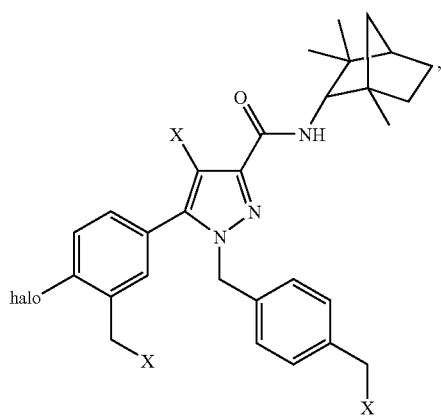

wherein X is H or substituted with

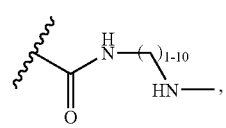

with at least one X being substituted; and halo is fluorine, chlorine, bromine, iodine, and stereoisomers and conjugable analogs thereof; and an agent having an affinity for a target binded thereto; and (b) introducing the conjugate to the sample.

21. The method of claim 20, wherein the agent is a signaling moiety.

22. The method of claim 20, wherein the agent is selected from an NIR dye, lanthanide chealate compound, or therapeutic agent.

23. The method of claim 20, wherein the sample is chosen from at least one of cells, tissue, cellular tissue, serum, cell extract, bodily fluids.

24. A method of imaging a molecular event in a sample, comprising:

(a) administering to said sample a probe having an affinity for a target, the probe comprising a compound of the following formula:

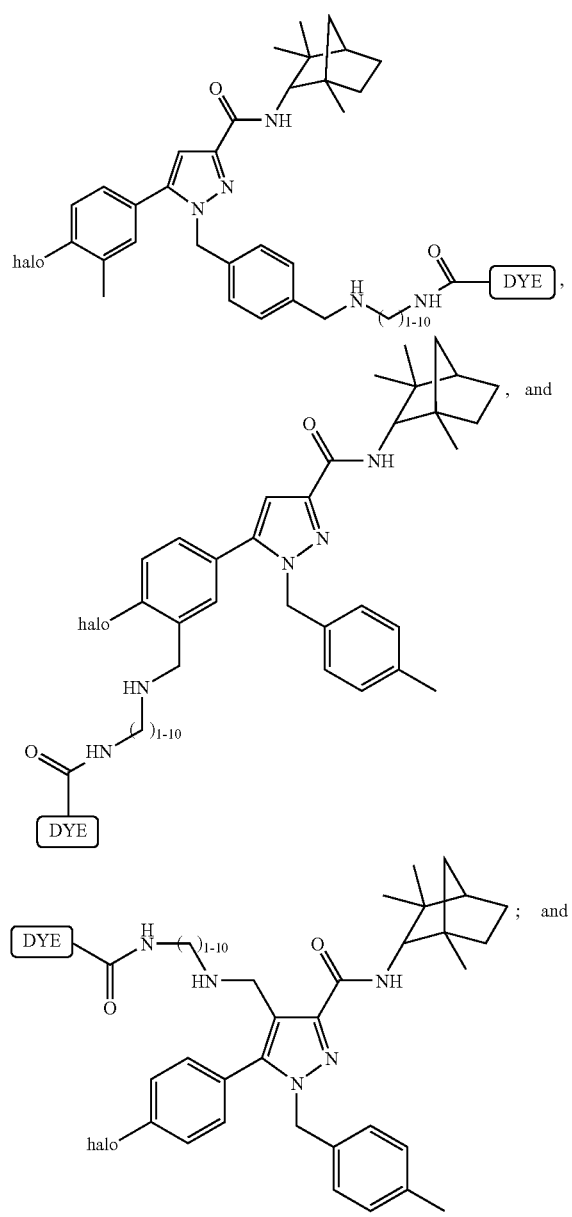

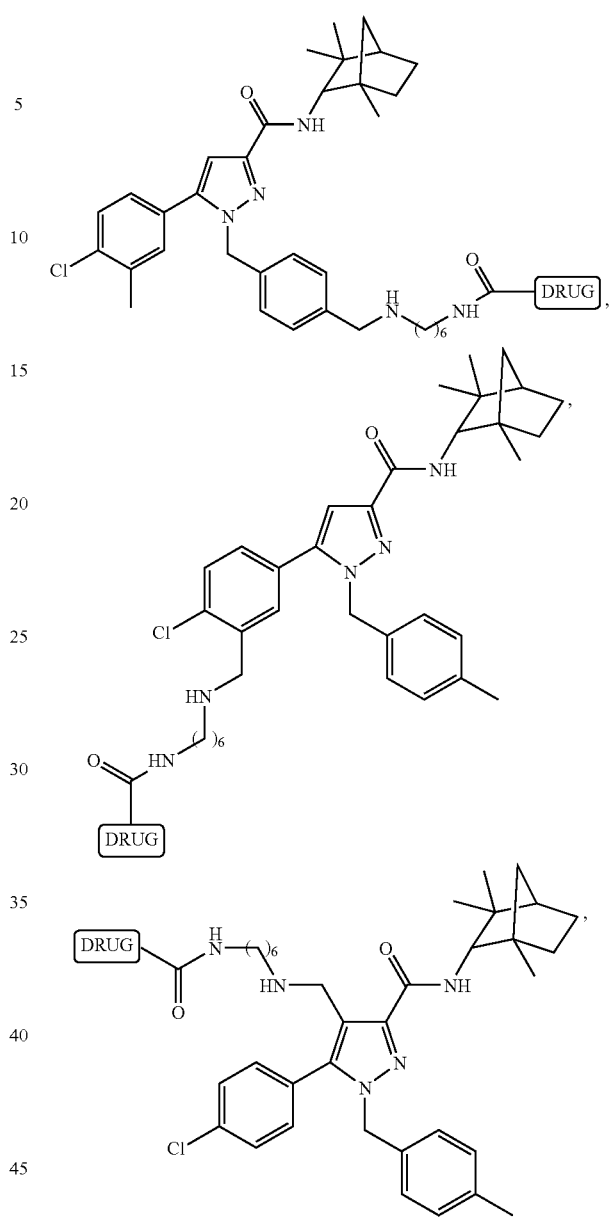

(b) detecting a signal from said probe.

25. The method of claim 24, wherein the sample is chosen from at least one of cells, tissue, cellular tissue, serum, cell extract, bodily fluids.

26. The method of claim 24, wherein DYE is an NIR dye or a conjugable form thereof.

27. The method of claim 24, further comprising the steps of (c) after a period of time from step (b), administering the probe to a second sample, (d) detecting a second signal; and (e) comparing the first signal with the second signal to determine the progress of a disease state.

28. A method of delivering a thearupeutic agent to a targeted cell, comprising administering to a patient in need thereof a compound of the following formula:

or a stereoisomer thereof.

29. The method of claim 28, wherein DRUG is a topoisomerase inhibitor or a conjugable form thereof.

30. The method of claim 29, wherein the topoisomerase inhibitor is selected from the group consisting of adriamycin, amsacrine, camptothecin, daunorubicin, dactinomycin, doxorubicin, eniposide, epirubicin, etoposide, idarubicin, mitoxantrone, teniposide, and topotecan; and conjugable forms thereof.

31. The method of claim 28, wherein DRUG is etopiside, or conjugable forms thereof.

32. The compound of claim 1, and a pharmaceutically acceptable carrier.

* * * * *